United States Patent
Debski et al.

(10) Patent No.: US 10,209,246 B2
(45) Date of Patent: Feb. 19, 2019

(54) METHOD FOR PERFORMING QUANTITATION ASSAYS

(71) Applicant: CURIOSITY DIAGNOSTICS SP. Z O.O., Warsaw (PL)

(72) Inventors: Pawel Rafal Debski, Warsaw (PL); Adam Warchulski, Milanowek (PL); Piotr Garstecki, Warsaw (PL)

(73) Assignee: CURIOSITY DIAGNOSTICS SP. Z.O.O. (PL)

( * ) Notice: Subject to any disclaimer, the term of this patent is extended or adjusted under 35 U.S.C. 154(b) by 245 days.

(21) Appl. No.: 14/411,303

(22) PCT Filed: Mar. 15, 2013

(86) PCT No.: PCT/EP2013/000805
§ 371 (c)(1),
(2) Date: Dec. 24, 2014

(87) PCT Pub. No.: WO2014/000834
PCT Pub. Date: Jan. 3, 2014

(65) Prior Publication Data
US 2015/0204858 A1    Jul. 23, 2015

(30) Foreign Application Priority Data

Jun. 26, 2012  (PL) ........................... 399673
Jul. 11, 2012  (PL) ........................... 399908
Nov. 19, 2012  (WO) .............. PCT/EP2012/004792

(51) Int. Cl.
*G01N 33/48* (2006.01)
*G01N 33/50* (2006.01)
*G01N 33/53* (2006.01)
*C12Q 1/6851* (2018.01)

(52) U.S. Cl.
CPC ....... *G01N 33/5306* (2013.01); *C12Q 1/6851* (2013.01)

(58) Field of Classification Search
None
See application file for complete search history.

(56) References Cited

U.S. PATENT DOCUMENTS

2014/0147908 A1  5/2014  Jakiela et al. ........... G01N 1/28

FOREIGN PATENT DOCUMENTS

| PL | 395776 | 2/2013 | ............... B01L 3/00 |
| PL | 395777 | 2/2013 | ............... B01L 3/00 |
| PL | 395778 | 2/2013 | ............... B01L 3/00 |
| PL | 398979 | 10/2013 | ............... B01F 13/00 |
| WO | WO2011090396 | 7/2011 | ............... B01L 3/00 |
| WO | WO2012049316 | 4/2012 | ............... C12Q 1/68 |

(Continued)

OTHER PUBLICATIONS

Vogelstein et al. Digital PCR. PNAS, vol. 96, 1999, pp. 9236-9241.*

(Continued)

*Primary Examiner* — Russell S Negin
(74) *Attorney, Agent, or Firm* — Hayes Soloway P.C.

(57) ABSTRACT

The present invention relates to a method for determining an estimate of a concentration of analyte particles E(C) as well as an apparatus for use in the inventive method, uses of the inventive method or the inventive apparatus, a sample holder and a kit for use in the inventive method.

15 Claims, 4 Drawing Sheets

(56) References Cited

FOREIGN PATENT DOCUMENTS

| WO | WO2012100198 | 7/2012 | ............. G01F 22/00 |
|----|--------------|--------|--------------------------|
| WO | WO2012109600 | 8/2012 | ............... C21Q 1/68 |
| WO | WO2013072069 | 5/2013 | ............... C12Q 1/68 |
| WO | WO2013160408 | 10/2013 | ................ B01L 3/00 |

OTHER PUBLICATIONS

International Search Report and Written Opinion issued in corresponding application No. PCT/EP2013/000805, dated Apr. 24, 2013 (12 pgs).

Kiss et al., "High-Throughput Quantitative Polymerase Chain Reaction in Picoliter Droplets," Analytical Chemistry, Vo. 80, No. 23, Dec. 1, 2008, pp. 8975-8981 (7 pgs).

Beer et al., "On-Chip, Real-Time, Single-Copy Polymerase Chain Reaction in Picoliter Droplets," Analytical Chemistry, vol. 79, No. 22, Nov. 15, 2007, pp. 8471-8475 (6 pgs).

Beer et al., "On-Chip Single-Copy Real-Time Reverse-Transcription PCR in Isolated Picoliter Droplets," Analytical Chemistry, vol. 80, No. 6, Mar. 15, 2008, pp. 1854-1858 (5 pgs).

Kreutz et al., "Theoretical Design and Analysis of Multivolume Digital Assays with Wide Dynamic Range Validated Experimentally with Microfluidic Digital PCR," Analytical Chemistry, vol. 83, No. 21, Nov. 1, 2011, pp. 8158-8168 (11 pgs).

Shen et al., "Multiplexed Quantification of Nucleic Acids with Large Dynamic Range Using Multivolume Digital RT-PCR on a Rotational SlipChip Tested with HIV and Hepatitis C Viral Load," American Chemical Society, 2011, 133, pp. 17705-17712 (8 pgs).

Korean Office Action (with translation) issued in application No. 10-2014-7016582, dated Mar. 22, 2017 (13 pgs).

Wagle et al., "High-Throughput Detection of Actionable Genomic Alterations in Clinical Tumor Samples by Targeted, Massively Parallel Sequencing," downloaded from cancerdiscovery.aacrjournals.org on Mar. 9, 2017. ©2012 American Association for Cancer Research (29 pgs).

Debski et al. "Rational Design of Digital Assays", Institute of Physical Chemistry, Polish Academy of Sciences, Kasprzaka, ACS Publications, 2015, Analytical Chemistry, 87, pp. 8203-8209, including Supporting Information pp. 1-20.

Debski et al., "Calibration-free assays on standard real-time PCR Devices," Scientific Reports, 7:44854, Dated Mar. 22, 2017 pp. 1-10, including Supporting information 19 pages.

* cited by examiner

METHOD FOR PERFORMING QUANTITATION ASSAYS

TECHNICAL FIELD

The present invention relates to a method for determining an estimate of a concentration of analyte particles E(C) as well as an apparatus for use in the inventive method, uses of the inventive method or the inventive apparatus, a sample holder and a kit for use in the inventive method.

BACKGROUND ART

Quantitative analytical assays are important in many fields of medical diagnostics and research where they are used to estimate quantitatively the concentration of analyte particles in samples.

In the prior art there are multiple standard (or "analogue") assays that use a known correlation between the amplitude of a measured signal (e.g. absorbance of light through a sample cell, electrical conductivity of the sample, time of passage of a sample through a porous bed, intensity of fluorescence, amplitude of force exerted on the sample, etc.) and the concentration of analyte particles in the sample. The estimate E(C) of the concentration C of the analyte particle is then retrieved as a calibrated function $f(A)$ of the amplitude A of the signal.

An example of a reaction that conforms to the above "analogue" requirements is quantitative PCR (or Real-Time PCR) that allows quantification of the measurable signal (i.e. the increase of the fluorescence from a fluorescent DNA stain). Knowing that the amplification of the presence of the analyte particle is geometrical, one can assess the initial number of DNA copies in the sample by analyzing kinematics of the signal measured at the end of every PCR cycle. The Real-Time PCR technique allows to determine the number of copies, or the concentration of the analyte, in a very wide range of concentrations (i.e. dynamic range ($\Omega$)), however, the precision of the measurement of this kind is significantly lower than for competitive quantitative PCR techniques, e.g. digital PCR techniques.

In Real-Time PCR (RT-PCR) a finite number of analyte particles in the inspected volume is sufficient to achieve a measurable signal, and the signal generally increases in time in a reproducible manner, so that it is possible to define a threshold value of the intensity of fluorescence from the inspected volume and measure the interval between the onset of amplification and the instant at which the intensity is equal the threshold value.

Analogue assays, based on RT-PCR technique, have found a wide variety of applications in biochemistry and diagnostics and is used as a 'golden standard' technique for concentration assessment. They present a range of advantages.

First of all, it requires a very small sample and no (or very simple) partitioning for assessment and easily determines relative changes of number of analyte particles/concentration of the analyte. Analogue PCR techniques are also relatively quick, as the whole analysis takes only up to one hour, and relatively robust via the detection based on the use of molecular probes.

However, the estimate of concentration of the target nucleic acids in the RT-PCR procedures is always done via referencing to the signal from an external calibrated reference sample containing a known concentration of the target. In practice, due to random and systematic changes in the choice of substrates, analyte particles, sensitivity of the sensor, condition of the apparatus, etc., calibration needs to be performed frequently. Importantly the accuracy of the estimate of concentration obtained via RT-PCR procedure depends on the quality of external calibration and cannot be assessed at the point of measurement.

In the prior art there are also known "digital" assays in which the concentration of analyte particles is established with the use of a statistical calculation on the basis of the number of binary (negative or positive) values of signals recorded from a set of independent partitions of the sample. In the digital assays usually the presence of a single, or a known threshold number of analyte particles, or a threshold concentration of analyte particles in the partition of the sample is amplified to a measurable "positive" signal ("positive" value). As the assays require strong amplification of the presence of the analyte particles, their key application lies in quantitative PCR or ELISA assays.

The development of the concept of the digital assay offered a new paradigm in analytical chemistry. It allows the absolute quantification without calibration of the experimental set-up. Also, it benefits from simplified laboratory routines, i.e. end-point measurement, and relatively plain mathematical tools needed to interpret the experimental results. The digital assays of the prior art are, however, also affected by limitations.

The maximum number of analyte particles M to be determined is directly proportional to the number N of compartments in the assay. In many applications and potential applications of diagnostic quantitation assays it is preferred that the span of the dynamic range ($\Omega = C^+/C^-$) (with $C^+$ representing the upper limit and $C^-$ representing the lower limit of estimated concentration of analyte particles in the assay) is large, for instance is equal to 1 million or more. To reach such a large span of the dynamic range in a standard digital PCR procedure, the sample must be partitioned into proportionally large number of compartments—in the said example—according to the state of knowledge in the field that overlooks unfavourably small precision at very small concentrations, into as many as 200,000 compartments or—actually—as shown in PCT/EP2012/004792, even 600,000 compartments. Partitioning a sample into such a huge number of compartments is—although possible—unfavourable, as such an assay requires specialized, complicated and expensive equipment to be performed. In particular, design of assays that aim to partition, amplify and inspect tens of thousands, or hundreds of thousands or millions of compartments require expensive technologies of micro-fabrication, automation and rapid and sensitive detection from multiple small volumes.

Furthermore, the precision and dynamic range achieved by the digital assays of the prior art cannot be independently tuned narrowing the range of applications and elevating the technical cost of the assays. Thus, it is not possible to obtain high precision (low standard deviation) in a narrow range of concentrations while using a small number N of compartments using digital assays of the prior art.

The prior art provides a solution to increase the span of the dynamic range of a digital assay and for reducing the number of compartments by combining classical digital quantitation assays with different dynamic ranges [Shen, F.; Sun, B.; Kreutz, J. E.; Davydova, E. K.; Du, W.; Reddy P. L.; Joseph, L. J.; Ismagilov, R. F., "Multiplexed Quantification of Nucleic Acids with Large Dynamic Range Using Multivolume Digital RT-PCR on a Rotational SlipChip Tested with HIV and Hepatitis C Viral Load", *J. Am. Chem. Soc.*, Article ASAP (X 2011)]. The solution relies on a simultaneously performed assay for multiple sets of compartments. The compartments belonging to each set have the same volume. In the cited example, $N_z=4$ sets are used with $N_j=160$ compartments each (j=1 to 4), with volumes of compartments equal to $v_j=1, 5, 25$ and $125$ nL in each of four sets. The procedure consists in i) dividing the samples into sets and compartments, ii) performing simultaneously signal amplification, iii) counting separately the number $K_j$ of positive values of signals in each of $N_z$ sets and iv) calculating the most probable initial concentration of analyte particles in the sample. The calculation is laborious and demanding, because of the requirement to calculate repeatedly the product $$\Pi_{j=1}^{N_z}\left\{\left[\frac{N_j!}{K_j!(N_j-K_j)!}\right][1-\exp(-v_jC)]^{K_j}[\exp(-v_jC)]^{N_j-K_j}\right\},$$

where the multiplication operator $\Pi_{j=1}^{N_z}$ denotes the product of $N_z$ terms calculated for each of $N_z$ compartment families, each term comprising the probability of observing $K_j$ positive values of signals from the j-th family. Computation of the result requires an iterative calculation of the said product for each tested, hypothetical value of C within the test dynamic range, until a value C is found for which the above product assumes the maximum. The above procedure must be repeated after each measurement of signals from the sample, which hinders the analysis of the test result, requires a sufficiently fast electronic device or elongates the time needed to obtain the estimate of the number of analyte particles in the sample. The above procedure would be in particular definitely unfavourable in the case of a large number (e.g. ten, or few tens, or hundred or more) of sets of compartments, characterised by that the compartments have the same volume within one set, but different volumes for each two different sets. Furthermore, WO 2012/100198 A2 discloses methods for performing digital measurements with varying volumes and, thus, widening the dynamic range.

Thus, the analogue assays typically provide for a facile method of quantitation on the basis of a single, or small number of measurements, yet they always require external calibration that constitutes an additional cost and hurdle in execution of the method. In contrast thereto, the digital assays typically provide absolute quantitation that does not require calibration. The drawback of the digital assays, however, is that for the requested precision of the estimate of concentration of analyte particles they typically require partitioning the sample into a large set of independent compartments that need to be treated chemically and physically and measured for the signal.

Accordingly, there exists a need for the provision of an improved quantitation method of analyte particles in a sample of predetermined volume, which allows for a reduced number of compartments and/or
allows for an adjustable precision and/or dynamic range and/or
does not require external calibration.

BRIEF DESCRIPTION OF THE INVENTION

The aforementioned needs are met in part or all by means of the claimed inventive subject matter. Preferred embodiments are in particular described in the dependent claims, the detailed description and/or the accompanying figures.

Accordingly, a first aspect of the present invention refers to a method for determining an estimate of a concentration of analyte particles E(C), wherein the analyte particles of a sample of predetermined volume are divided into a number (N) of two or more compartments, at least part of the analyte particles that are present in any of the (N) compartments provide for a measurable signal and the estimated concentration of analyte particles E(C) is a function of the measured signals, characterized in that the method comprises or consists of a) measuring a signal from two or more of the (N) compartments and assigning to at least part, preferably all compartments a value $(k_i)$, wherein (i) represents the index number of the compartment represented by an integer 0 to N−1 and compartment (i) is assigned a first value $(k_i)$, if the compartment (i) comprises or consists of a predetermined threshold number of analyte particles $(m_{tr_i})$ or a predetermined threshold concentration of analyte particles $(c_{tr_i})$, preferably one, two, three or more analyte particles in a compartment, and compartment (i) is assigned a second value $(k_i)$, if the compartment (i) comprises or consists of less than the number or concentration of analyte particles indicating the first value, b) determining a value $(\tau_i)$ for two or more of the (N) compartments respectively based on one or more measurements of signals in compartment (i) and (i) represents the index number of the compartment represented by an integer 0 to N−1, wherein the values $(\tau_i)$ depend on the number of analyte particles in the compartment (i) and comprise univocal functions of the number of analyte particles in compartment (i) and wherein at least for one compartment thereof a value $(k_i)$ is assigned according to step a), and c) determining the estimate of concentration of analyte particles E(C) as a function of part or all values $(k_i)$ assigned in step a) and part or all values $(\tau_i)$ assigned in step b).

A second aspect of the present invention refers to an apparatus for use in determining a concentration of analyte particles in accordance with the inventive method, characterized in that the apparatus is configured to a) measuring a signal from two or more of the (N) compartments and assigning to at least part, preferably all compartments a value $(k_i)$, wherein (i) represents the index number of the compartment represented by an integer 0 to N−1 and compartment (i) is assigned a first value $(k_i)$, if the compartment (i) comprises or consists of a predetermined threshold number of analyte particles $(m_{tr_i})$ or a predetermined threshold concentration of analyte particles $(c_{tr_i})$, preferably one, two, three or more analyte particles in a compartment, and compartment (i) is assigned a second value $(k_i)$, if the compartment (i) comprises or consists of less than the threshold number or concentration of analyte particles indicating the first value, b) determining a value $(\tau_i)$ for two or more of the (N) compartments respectively based on one or more measurements of signals in compartment (i) and (i) represents the index number of the compartment represented by an integer 0 to N−1, wherein the values $(\tau_i)$ depend on the number of analyte particles in the compartment (i) and comprise univocal functions of the number of analyte particles in compartment (i) and wherein at least for one compartment thereof a value $(k_i)$ is assigned according to step a), and c) determining the estimate of concentration of analyte particles E(C) as a function of part or all values $(k_i)$ assigned in step a) and part or all values $(\tau_i)$ assigned in step b).

A third aspect of the present invention refers to the use of the inventive method or the inventive apparatus for
a) reducing the total number (N) of compartments comprising the predetermined sample volume and/or
b) adjusting the precision and/or dynamic range and/or
c) eliminating the need of external calibration.

A fourth aspect of the present invention refers to a sample holder for use in an inventive method for determining a concentration of analyte particles, characterized in that the sample holder is configured to
a) comprising or consisting of a predetermined number (N) of compartments wherein the number (N) is smaller or equal to the value of the function $$N_{MAX} = B \cdot \ln\left(\frac{C^+}{C^-}\right)/\sigma_{MAX}^2$$

wherein (B) represents a real number being the integer 1 or less, preferably 0.5 or less, more preferably 0.2 or less, further more preferably 0.1 or less, wherein ($C^+$) represents a predetermined upper limit of the interval of concentration (C) to be estimated by the method, wherein ($C^-$) represents a predetermined lower limit of the interval of concentration (C) to be estimated by the method, herein ($\sigma_{MAX}$) represents a predetermined maximum allowable relative standard deviation of the estimate of concentration E(C) of analyte particles, wherein $C^- < C < C^+$, and
b) wherein the (N) compartments are configured to comprising the predetermined sample volume with a predetermined modulation factor ($z_i$), wherein ($z_i$) is a function of volumes ($v_i$) and dilution factors ($d_i$) of the sample in at least part of or all of the (N) compartments so that at least part of or all of the two or more of the (N) compartments can comprise or consist of different sample volumes ($v_i$) and/or different dilution factors ($d_i$) of the sample, wherein (i) represents an index number of the (N) compartments represented by the integers 0 to N−1, and wherein ($v_i$) represents the volume and ($d_i$) represents the dilution factor of the sample in the compartment (i).

A fifth aspect of the present invention refers to a kit comprising the inventive sample holder and one or more reagents suitable for amplifying at least part of analyte particles comprised in the compartments of the sample holder to a measurable signal and optionally one or more suitable diluents for determining a concentration of analyte particles, preferably for determining the concentration of analyte particles in accordance with the inventive method.

DETAILED DESCRIPTION OF THE INVENTION

Figure 1A:
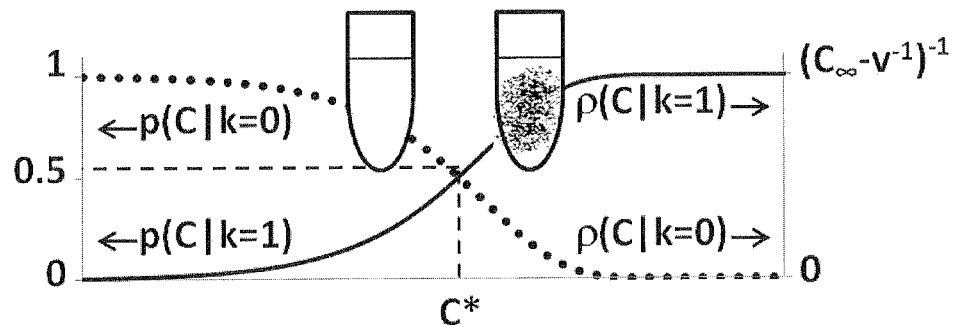
FIGS. 1a), 1b) and 1c): Graphs displaying the probabilistic information about the concentration of analyte particles based on the digital measurement.

As described in detail below, the present inventors have unexpectedly found out that it is possible to combine the information from digital recordings from a set of compartments with the analogue measurements from a set of compartments of compartments containing the sample of predetermined volume in accordance with the inventive method. The inventive method provides thus useful advantages that were not possible in the state of art, these including: the possibility to auto-calibrate each assay for its own chemistry and method of treatment instead of an external calibration that could be off-set and introduce a systematic error in the accuracy of the estimate, the ability to extract maximum information from analogue measurements by calibrating them with the digital measurements that are absolute in nature, the ability to extract information about the characteristics of the specific reaction undergoing in the given assay and about the precision and errors introduced by the apparatus. Importantly, the present invention allows for a favorable and significant reduction of the number of separate compartments into which the sample needs to be partitioned in order to achieve the required precision and dynamic range of the assay.

The present invention describes assays, apparatus and sample holders that take advantage of an innovative method of analysis of sets of digital and analogue values determined from sets of independent partitions of the sample (steps a) and b) of the inventive method). The digital value ($k_i$) may represent a first "positive" value reflecting the presence of at least a threshold number ($m_{tr_i}$) or concentration ($c_{tr_i}$) of analyte particles in a compartment (i), or a second "negative" value reflecting the presence of none or less than the threshold number ($m_{tr_i}$) or concentration ($c_{tr_i}$) of analyte particles in the compartment (i). The analogue value ($\tau_i$) from a compartment (i) may inventively either be determined via a direct measurement of a physical quantity, or an appropriate rescaling of a direct measurement of a physical quantity or via an appropriate mathematical calculation on the basis of a set of measurements. For example, the analogue value ($\tau_i$) may inventively be determined by interpolation or extrapolation or a different, known to those skilled in the art, mathematical procedure on the basis of a set of measurements conducted on the compartment (i). Steps a) and b) of the inventive method can be conducted with the same apparatus or with different apparatus. It is also possible that from one measurement step both values ($k_i$) and ($\tau_i$) can be determined.

The term "compartment" in the meaning of the present invention may comprise any analyte particle of the sample or of the amplification mixture that is effectively isolated from the rest of the sample during the amplification procedures and measurement of the signals. It is also possible to use the present invention in the case when the analyte article in compartment (i) is not completely isolated (spaced) from the rest of the sample or amplification mixture, but the transport of material between the compartment and the rest of the sample during the amplification procedures and/or measurement is known. In particular the term "compartment" in the meaning of the present invention may comprises separate sample volumes as reaction space as well as any other suitable form of isolated reaction space. For example, it is possible to conduct digital assays not only in separate volume compartments, but on a set of colloidal particles, each configured to adsorbing the analyte particles of interest on its surface. In the latter case the colloidal particle would be regarded as compartment in accordance with the present invention. Thus, the analyte particles of the predetermined sample volume may be inventively partitioned into a set of two or more of the number (N) compartments, i.e. a set of two or more separate "containers" or "agents" or "carriers".

With respect to the present invention the term "threshold number ($m_{tr_j}$) of analyte particles" or "threshold concentration ($c_{tr_j}$) of analyte particles" means that the value of the "threshold number ($m_{tr_j}$) of analyte particles" or "threshold concentration ($c_{tr_j}$) of analyte particles" can independently from each be assigned to the compartments (i) of the number (N) of compartments, i.e. the values of the "threshold number ($m_{tr_j}$) of analyte particles" or "threshold concentration ($c_{tr_j}$) of analyte particles" for the compartments (i) can all be different or can all be the same or for a part of the compartments (i) the values differ and for the rest values are the same. In a preferred embodiment of the present inventive method, the values of the "threshold number ($m_{tr_j}$) of analyte particles" or "threshold concentration ($c_{tr_j}$) of analyte particles" are functions solely of the method of division of the analyte particles between the compartments (i) and/or of a subsequent treatment of the compartments (i) and/or of the method of signal measurement in the compartments (i), more preferably the values of the "threshold number ($m_{tr_j}$) of analyte particles" or "threshold concentration ($c_{tr_j}$) of analyte particles" are functions solely of the combination of the method of division of the analyte particles between the compartments (i) and of a subsequent treatment of the compartments (i) and of the method of signal measurement in the compartments (i).

With respect to the inventive determination of the estimate concentration E(C) of analyte particles any common statistical method for determination of estimate concentration E(C) of analyte particles in quantitative assays can be used. Preferred embodiments of the present invention are disclosed further down in the following description.

The inventive determination of estimate of concentration E(C) of analyte particles generally comprises determination of estimate of concentration E($C_{sample}$) of analyte particles in the sample as well as the determination of estimate of concentration E($C_{reservoir}$) of analyte particles in the reservoir or the determination of estimate of concentration E($C_{specimen}$) of analyte particles in the specimen, which is in detail explained in the following. The estimate of concentration E(C) is a function of the estimated number E(M) of analyte particles in the respective sources, e.g., sample volume, reservoir volume or specimen volume. Accordingly, in case estimate of concentration E(C) of analyte particles is used with respect to the present invention the term generally refers to the estimate of concentration E($C_{sample}$) of analyte particles in the sample, the estimate of concentration E($C_{reservoir}$) of analyte particles in the reservoir and the estimate of concentration E($C_{specimen}$), unless stated otherwise.

Thus, in a preferred embodiment the present invention relates to the determination of the concentration of analyte particles in the sample E($C_{sample}$)=E(M)/$V_{sample}$, wherein E(M) is the estimated number of analyte particles in a sample of volume $V_{sample}$. In the procedure the volume of the sample is partitioned and mixed with appropriate volumes of reagents, to allow for amplification of the presence of analyte particles in the compartments to a measurable signal and to obtain the desired volumes $v_i$ and dilution factors $d_i=(m_i/v_i)/(M/V_{sample})$, where $m_i$ is the estimated number of analyte particles in i-th compartment. The quotients (M/$V_{sample}$) and ($m_i/v_i$) can be coded as concentrations of analyte particles in the sample ($C_{sample}$) and of analyte particles in the i-th compartment ($C_{sample}$), yet as there is a finite number of analyte particles in the sample, and placement of a analyte particle in one compartment affects the probability of finding it in another compartment it has to be understood that these are not true concentrations as they only represent the estimated number of analyte particles scaled by the volume of either sample or compartment. As will be discussed below, the appropriate—and known in the prior art—approach to the analysis of the signals from compartments is based on the dependant random variables of placement of analyte particles in the compartments. Such analysis yields the estimated number E(M) of analyte particles in the sample, that can be represented as the estimated concentration E($C_{sample}$) of analyte particles in the sample.

In an alternative preferred embodiment it is preferred that the sample volume $V_{sample}$ containing the analyte particles of interest is prepared (e.g. by isolation or purification of analyte particles) from a volume $V_{specimen}$ of a specimen. In such a case, the estimate E(M) of the number of analyte particles in the sample is the same as the estimate of the number of analyte particles in the specimen. These can be represented either by the estimated concentration of analyte particles in the sample E($C_{sample}$)=E(M)/$V_{sample}$ or by estimated concentration of analyte particles in the specimen E($C_{specimen}$)=E($C_{sample}$)($V_{sample}$/$V_{specimen}$)=E(M)/$V_{specimen}$.

In an alternative preferred embodiment of the present invention the volume $V_{specimen}$ of the specimen may be taken from a much larger volume of a reservoir (e.g. an organism, or environment). It may be then of interest, and is possible with the use of the present invention, to estimate the concentration E($C_{reservoir}$) of analyte particles in the reservoir. In such a case the placement of analyte particles in the compartments formed by partitioning and optionally also diluting the sample is treated as a set of independent random variables. The probability of finding a analyte particle in any given compartment is, within this approach, only a function of the volume of the compartment, the dilution ratio of the sample in the compartment and of the concentration $C_{sample}$ of analyte particles in the sample which is in turn equal to the concentration of analyte particles in the reservoir, scaled by the appropriate quotients of volumes of sample and of specimen. As a result of calculation based on the signals from the compartments the invention allows to retrieve the estimate of concentration of analyte particles in the sample E($C_{sample}$). The estimate of the concentration of analyte particles in the reservoir is the same as the estimate of concentration of analyte particles in the specimen: E($C_{reservoir}$)=E($C_{specimen}$)=E($C_{sample}$)($V_{sample}$/$V_{specimen}$).

Alternatively, the estimate of the concentration E($C_{reservoir}$) of the analyte particles in the reservoir can also be preferably determined by transforming the estimate E(M) of the number of analyte particles in the sample obtained from a calculation based on a distribution of dependent variables. In most general terms, the probability distribution of concentration in the reservoir $\rho(C_{reservoir})$ is equal to an integral transform of the distribution of probability of the number of analyte particles in the sample $\rho(M/V_{sample})$. In a simplified protocol, the estimate of E($C_{reservoir}$) can preferably be determined by multiplying E(M)/$V_{sample}$ by a correction function $f_{corr}$(E(M)) and by scaling it by the quotient $V_{sample}$/$V_{specimen}$.

In a preferred embodiment of the inventive method values $(m_{min,\tau_i})$ for the minimum number or the values $(c_{min,\tau_i})$ for the minimum concentration of the analyte particles are assigned to at least one or more of the compartments (i) on the basis of the set of values $(m_{tr_j})$ or of the set of values of $(c_{tr_j})$ and at least two or more of the analogue values $(\tau_i)$, and optionally values $(m_{min,k_j})$ of the minimum number or the values $(c_{min,k_j})$ of the minimum concentration of the analyte particles are assigned to at least one or more of the compartments (i) on the basis of the and the positive digital first values (e.g., $k_i=1$), and optionally values $(m_{max,k_j})$ of the maximum number or values $(c_{max,k_j})$ of the maximum concentration of the analyte particles are assigned to at least part or all of the compartments (i) on the basis of the set of values $(m_{tr_j})$ or of the set of values of $(c_{tr_j})$ and at least two or more of the negative digital second values (e.g., $k_i=0$) and/or optionally values $(m_{max,\tau_i})$ of the maximum number or values $(c_{max,\tau_i})$ of the maximum concentration of the analyte particles are assigned to at least part or all of the compartments (i) on the basis of the set of values $(m_{tr_j})$ or of the set of values of $(c_{tr_j})$ and at least two or more of the analogue values $(\tau_i)$.

In case the values $(m_{min,\tau_i})$ for the minimum number or the values $(c_{min,\tau_i})$ for the minimum concentration of the analyte particles and/or the values $(m_{min,k_j})$ for the minimum number or the values $(c_{min,k_j})$ for the minimum concentration of the analyte particles and/or values $(m_{max,k_j})$ for the minimum number or the values $(c_{max,k_j})$ for the maximum concentration of the analyte particles and/or values $(m_{max,\tau_i})$ for the minimum number or the values $(c_{max,\tau_i})$ for the maximum concentration of the analyte particles have been assigned to at least one or more of the compartments (i), the determination of the estimate E(C) of concentration C of the analyte particles of step c) of the inventive method is preferably determined as a function of at least a part or all values $(m_{min,\tau_i})/(c_{min,\tau_i})$ and/or values $(m_{min,k_j})/(c_{min,k_j})$ and/or values $(m_{max,k_j})/(c_{max,k_j})$ and/or and $(m_{max,\tau_i})/(c_{max,\tau_i})$ in compartment (i) and the probability distribution $(p_i(m_i))$ of compartment (i) containing initially the number (me) of analyte particles or probability distributions $(p_i(c_i))$ of compartment (i) containing initially the concentration $(c_i)$ of analyte particles, wherein the probability distributions $p_i(m_i)/p_i(c_i))$ are predetermined functions of the concentration C of analyte particles in the sample.

The use of assigning the values $(m_{min,\tau_i})/(c_{min,\tau_i})$ and/or values $(m_{min,k_j})/(c_{min,k_j})$ and/or values $(m_{max,k_j})/(c_{max,k_j})$ and/or and $(m_{max,\tau_i})/(c_{max,\tau_i})$ for compartments (i) and determining the estimate concentration E(C) of concentration C of the analyte particles of step c) of the inventive method is preferred, as there exists a probability that compartment (i) may be assigned a positive digital first value $(k_i)$ although less than the threshold number or concentration of particles is present in compartment (i) or vice versa that compartment (i) may be assigned a negative digital second value $(k_i)$ although at least the threshold number or concentration of particles is present in compartment (i). Accordingly, the precision of the inventive method can furthermore be increased.

In the above description of the preferred embodiment of the inventive method, the values $(m_{min,\tau_i})/(c_{min,\tau_i})$, $(m_{min,k_j})/(c_{min,k_j})$, $(m_{max,k_j})/(c_{max,k_j})$ and $(m_{max,\tau_i})/(c_{max,\tau_i})$ are all indexed with the index i that indexes the compartment, while the letters $\tau$ and k, signify that the values were calculated either as functions of the analogue and digital signals, or without the use of analogue signals, respectively. All the values may of course also be functions of the properties of compartments $(\Gamma_i)$ and of treatment $(T_i)$, as described in the present invention.

In case the analyte particles to be measured in accordance with the present invention do not provide as such a measurable signal, it is according to the inventive method preferred to amplify the measured signal correlated with the analyte particles so that at least part of the particles, preferably all of the particles provide for a measurable signal. A suitable measurable signal can be any signal which can be detected, e.g. visually and/or by other suitable means. The measuring methods in step a) and/or step b) of the inventive method may be conducted with suitable means, preferably with detectors, which can detect physical properties selected from the group consisting of light excitation with respect to colour or intensity, e.g. in UV range, visible range and/or IR range; light absorbance, e.g. in UV range, visible range and/or IR range; electrical conductivity; time of passage of analyte particles through a suitable matrix; amplitude of force exerted on the sample; or any other suitable measurement method.

In a preferred embodiment of the inventive method the analyte particles may be labeled with a suitable component, e.g. a reporter molecule, which binds, forms complexes or interacts with the analyte particles in such a way that they provide for a measureable signal as disclosed above, e.g. excite light of specific wavelength and/or electric conductivity upon suitable excitation, preferably they exhibits fluorescence (up and down converting), exhibit light in the infrared (IR) range (near and/or far infrared wavelength, NIR/FIR), or exhibit electric conductivity. Reporter molecules in particular suitable for use in any of the hereinafter mentioned amplification methods are commonly known. In a preferred method two reporter molecules can be used, which compete for a single binding site of the analyte particle to be determined and, thus, furthermore extend the dynamic range of the inventive method. An example of suitable reporter molecules is given in WO 2012/049316 A1, wherein the different reporter molecules (markers) are used to interact (directly or indirectly) with the analyte particles of the sample, wherein the reporter molecules are preferably nucleic acid molecules, e.g. oligonucleotides. Such reporter molecules are preferably used in proximity probe-based detection assays and the disclosure of WO 2012/049316 A1 concerning the suitable reporter molecules (markers) is incorporated herein in its entirety.

The inventive method can be used to design assays for quantitation techniques amplifying the presence of a suitable analyte particle to a measurable signal, preferably wherein the analyte particles are amplified by means of Polymerase Chain Reaction (PCR), more preferably comprising cyclic temperature variation; loop-mediated isothermal amplification (LAMP); rolling circle amplification (RCA); cascade rolling circle amplification (Cascade RCA); helicase-dependent amplification; nucleic acid sequence based amplification (NASBA); nicking enzyme amplification reaction (NEAR); (single-molecule) enzyme-linked immunoabsorbent assay [(digital) ELISA]; or electrochemiluminescence immunoassay (ECLIA); competitive or non-competitive immunoassays; chemical chain reactions; avalanche reactions; or any other procedure for amplification of the presence of a analyte particle to a measurable signal, wherein the amplitude of the signal is a univocal function of the concentration of analyte particles; or a combination thereof. In particular the present inventive method can be applied to design an assay for the current real-time PCR apparatus. The aforementioned amplification methods are known in the prior art and a person skilled in the art will readily know which suitable one or more reagents and optionally one or more diluents can be used.

The inventive method is generally applicable to quantify suitable analyte particles in a predetermined sample volume, preferably selected from the group comprising or consisting of nucleic acids, peptides, proteins, receptors, enzymes, bacteria, pesticides, drugs, steroids, hormones, lipids, sugars, vitamins or any other suitable analyte particles, such as nanoparticles or colloids, or combinations thereof.

The inventive method is generally applicable to assays, wherein the signals in compartment (i) are measured in step a) and step b) with the same or with different measurements in the same or different apparatus. The measuring methods in step a) and/or step b) may be conducted with the same or different suitable means, preferably with detectors, which can detect physical properties selected from the group consisting of light excitation with respect to colour or intensity, e.g. in UV range, visible range and/or IR range; light absorbance, e.g. in UV range, visible range and/or IR range; electrical conductivity; time of passage of analyte particles through a suitable matrix; amplitude of force exerted on the sample; or any other suitable measurement method. The assignment and determination of the respective values ($k_i$) in step a) and ($\tau_i$) in step b) of the inventive method can also be conducted by suitable means, in particular common apparatus, preferably comprising a computer with a memory device configured with executable instructions stored thereon, the instructions—when executed by a processor—provide for assigning the respective values ($k_i$) in step a) and ($\tau_i$) in step b) of the inventive method.

Furthermore the number (N) of separate compartments to be used with respect to the inventive method according to the first aspect of the present invention is preferably determinable based on the function, wherein the number (N) is smaller or equal to the value of the function $$N_{MAX} = B \cdot \ln\left(\frac{C^+}{C^-}\right)/\sigma_{MAX}^2$$

wherein (B) represents a real number equal to 6 or less, preferably 1 or less, more preferably 0.5 or less, even more preferably 0.2 or less, or even more preferably 0.1 or less, wherein ($C^+$) represents an upper limit of the interval of concentration (C) to be estimated by the method wherein ($C^-$) represents a lower limit of the interval of concentration (C) to be estimated by the method, wherein ($\sigma_{MAX}$) represents a maximum allowable relative standard deviation of the estimate of concentration (C) of analyte particles, wherein $C^- < C < C^+$.

With respect to the aforementioned determination of number (N) of compartments, wherein the number (N) represents an integer 0 to N−1, the integer is preferably larger than the real result of the function, preferably wherein the integer is the smallest integer larger than the real result of the function.

The inventors have observed, that the number of sample compartments used to determine the concentration using the above algorithm scales linearly with the parameter $\ln \Omega/\sigma_{MAX}^2$. This behavior was also observed for the algorithms based only on the digital signals as with respect to the prior art digital PCR assays (Ismagilov or PCT/EP2012/004792). The coefficient (B) of this proportionality can be a measure of effectiveness of the partitioning. In accordance with the prior art, however, coefficient (B) with respect to the digital multivolume assays of the prior art from Ismagilov cannot be 6 or smaller or with respect to PCT/EP2012/004792 cannot be 1 or smaller, while with respect to the presented inventive method the coefficient (B) can be 6 or less, preferably 1 or less, more preferably 0.5 or less, even more preferably 0.2 or less and in an even more preferred embodiment 0.1 or less. Accordingly, the inventive method provides an improved quantification assay which allows for further reducing the number of compartments in light of the prior art digital quantification assays.

In case the number (N) of separate compartments is determined in accordance with aforementioned function $$N_{MAX} = B \cdot \ln\left(\frac{C^+}{C^-}\right)/\sigma_{MAX}^2,$$

a modulation factor ($z_i$) is determined, wherein ($z_i$) is a function of volumes ($v_i$) and dilution factors ($d_i$) of the sample in at least part of or all of the (N) compartments and partitioning the sample into the (N) compartments, wherein at least part of or all of the two or more of the (N) compartments comprise or consist of different sample volumes ($v_i$) and/or different dilution factors ($d_i$) of the sample, wherein (i) represents an index number of the (N) compartments represented by the integers 0 to N−1, and wherein ($v_i$) represents the volume and ($d_i$) represents the dilution factor of the sample in the compartment (i). Thus, the inventive method provides an improved quantification assay which allows for reducing the number of compartments and at the same time allows for assessment of a wide dynamic range and a high precision, without the need of external calibration.

In accordance with the preferred inventive use of the partitioning the sample volume in accordance with the aforementioned modulation factor ($z_i$), the modulation factor ($z_i$) is preferably determined based on a well defined power sequence, an exponential sequence, preferably a geometrical sequence; a polynomial sequence or based on a distribution in the set of compartments, preferably predetermined by Gaussian distribution or a combination thereof. Further preferred embodiments are also disclosed in the following description. More generally, the set of values of the products $v_i d_i$ can be determined by any function that is non-uniform over the range of variation of the index i and may be a function of the dynamic range of the assay, of the precision of the assay and of other important parameters of the assays and its technical realization.

Although the inventive method can be conducted wherein all compartments have the same volume ($v_i$) and dilution factor ($d_i$), in a preferred embodiment of the inventive method 1%, preferably 5%, more preferably 25%, even more preferably 50%, even more preferably 75% and most preferably 100% of the (N) compartments differ from each other by the value of the modulation factor ($z_i$). The more of the (N) compartments differ from each other by the value of the modulation factor ($z_i$), the broader is the range of concentrations of analyte particles in the sample that can be assayed. In preferred embodiments the inventive method teaches how to use sets of compartments differing their volume and/or dilution factor.

In accordance with the present invention the partitioning of the predetermined sample volume into N compartments can be conducted by any suitable common method. In a preferred method, the sample is partitioned according to the determined number N of compartments and according to the determined modulation factor $z_i$ by suitable means of pipetting the sample volume; by suitable means of droplet generation by microfluidic systems, preferably active and/or passive droplet generation; by suitable means of digital microfluidic techniques (also referred to as "electro-wetting on dielectric" EWOD), or by any other suitable method for obtaining the partitioned set of compartments (such as, e.g. disclosed in WO 2012/109600 A2, which disclosure in context with partitioning is incorporated herein in its entirety). The partitioning can also be performed by linking the particles of analyte particles with colloidal or nanoscopic particles or by isolating subvolumes of the sample or amplification mixture for the purpose of amplification and/or measurement of the signal.

With respect to the pipetting technique a common serial dilution through repetitive mixing, splitting and adding diluents (suitable buffers) generally enables the inventive partitioning of the predetermined sample volume according to the determined number N of compartments and according to the determined modulation factor $z_i$. As an example, the first compartment of the series may comprise a certain volume $v_0$ of the predetermined sample volume with a concentration $C_0$, then the second compartment of the series comprises a fraction x of the predetermined sample volume which is then diluted by adding suitable diluents to reach the volume $v_0$, so that the second compartment comprises $C_1=C_0 x^1$. Repeating this procedure yields a geometric progression of concentrations $C_i=C_0 x^i$. A suitable apparatus for conducting such a pipetting procedure is for example a hand pipette, or any of the commonly known robotic pipetting stations, or apparatus dedicated to pipetting ultra small volumes, as for example the Mosquito apparatus marketed by TTP Labtech.

In general the aforementioned pipetting method can also be used to prepare a set of compartments presenting a geometric progression of the estimated number of analyte particles: $(d_i v_i)/(d_0 v_0) = z_i = x^i$ by modulating either the concentration, or the volume of each compartment, or both, in any sequence or combination.

With respect to the microfluidic system technique all suitable common techniques can be applied to the present invention, in particular, common active droplet microfluidic systems and passive microfluidic systems, which enable the inventive partitioning of the predetermined sample volume in accordance with the determined number N of compartments and according to the determined modulation factor $z_i$.

With respect to the active droplet microfluidic system technique the present inventors have in particular developed a range of techniques for on-demand execution of operations on microdroplets in microfluidic chips. The operations include i) generation of a small droplet of precisely determined volume, ii) translating the droplet, iii) merging droplets, iv) splitting droplets. These operations allow executing practically any protocol of dilutions and inventive partitioning. The aforementioned active microfluidic technique has been disclosed in particular in the following patent applications PCT/PL2011/050002 "System and method for automated generation and handling of liquid mixtures", filed 21 Jan. 2011 and the subsequent national applications; PL395776 "Spósb dzielenia kropel na żądanie w złączu mikroprzepływowym" filed 2011 Jul. 27; PL395777 "Sposób dzielenia kropel na żądanie w mikroprzeptywowym" filed 2011 Jul. 27; PL395778 "Sposób dzielenia kropel na żądanie w złączu mikroprzep/lywowym" filed 2011 Jul. 27, wherein the content of each application in relation to the active microfluidic techniques is incorporated herein with respect to the present invention in their entirety.

With respect to the passive microfluidic systems (traps) the present inventors (for Scope Fluidics) in particular have developed a system and method for execution of precise operations on droplets in a passive manner. The concept is based on the construction of well geometrically defined 'traps' in the microfluidic channels. The traps, depending on their exact geometry, can i) trap a droplet smaller than a given volume and hold it in place, ii) trap a droplet of precisely set volume and hold it in place, iii) exchange a portion of liquid in the trapped droplet (i.e. accept a small additional volume and release the same volume of the original mixture), iv) trap, wait for arrival of a new droplet, then merge them and release, v) trap, wait for arrival of subsequent drop, then release just the first, while locking the second, etc. These functionalities allow building a lot of different liquid handling protocols, which can be used in accordance with the present invention. The aforementioned passive microfluidic technique (so called "TRAPS" system and method) has been disclosed in particular in the following patent application [PL-398979 "Urządzenie mikroprzepływowe i układ mikroprzepływowy obejmujący jedno lub więcej urządzeń mikroprzepływowych" filed 2012 Apr. 25], wherein the content thereof in relation to the passive microfluidic technique is incorporated herein with respect to the present invention in its entirety.

Furthermore, the well established technological platform for manipulations of droplets on planar substrates called either 'digital microfluidics' or 'electro-wetting on dielectric' (EWOD) enables the inventive partitioning of the predetermined sample volume in accordance with the determined number N of compartments and according to the determined modulation factor $z_i$. The digital microfluidic technique/electro-wetting on dielectric (EWOD) technique allows to generate drops on demand, move them, merge, mix and split them.

The predetermined sample volume is in accordance with the present invention partitioned into N compartments, wherein any common sample holder suitable for holding the separate volumes so that the volumes can be further processed and/or analyzed in accordance with the inventive digital assays can be used.

In a preferred embodiment the predetermined sample volume is partitioned into an inventive sample holder according to the fourth aspect of the present invention. The sample holder of the present invention can comprise e.g. suitable test tubes, arrays of wells on a microarray, or a microfluidic chip, a microfluidic chip configured to generating droplets as well as other commercially available or otherwise generally known devices capable of holding discrete volumes suitable for carrying out the inventive method. In a furthermore preferred embodiment the predetermined sample volume is partitioned using the inventive kit in accordance with the fifth aspect of the present invention. All preferred embodiments of the fourth and fifth aspect of the present invention can independently from each other be combined with the present inventive method.

The inventive method according to the first aspect of the present invention can preferably be carried out as follows:
  i. The sample supposed to comprise the analyte particle is divided into separate compartments, whereby the number of analyte particles in the compartments are stochastic variables determinable with a known or expected probability distribution $(p_i(m_i))$. For example, for a simple division of a uniform solution or suspension, the number of analyte particles may be predetermined by a Poissonian distribution $p_i(m_i)=e^{-Cd_iv_i}(Cd_iv_i)^{m_i}/m_i!$. Alternatively, if compartments are treated as non-independent (i.e. the distribution of analyte particles in one compartment affects the distribution of analyte particles in other compartments), this number may be predetermined by a combinatory equation. More generally, the number of analyte particles may be predetermined by different probability distributions that depend on the method of sample division into the compartments, or chemical or physical mechanisms affecting allocation of analyte particles to the compartments. Thus, the probability distribution $(p_i(m_i))$ of the number of analyte particles in compartment (i) may be a function of properties $(\Gamma_i)$ of compartment (i) and of the determinable concentration of analyte particles in compartment (i). The properties $(\Gamma_i)$ of compartment (i) comprise or consist of the dilution factor $(d_i)$ of the sample in compartment (i) and/or the volume $(v_i)$ of the sample in compartment (i) and/or of the surface to volume ratio of compartment (i) and/or by distributions resulting from other mechanisms of deposition, e.g. ballistic or more general forced deposition of analyte particles at interfaces or in compartments. For example, the probability distribution $p_i(m_i,\{d_i,v_i\})$ could be affected by adsorption of analyte particles to interfaces, and thus by the surface to volume ratio of the compartment, or by distributions resulting from other mechanisms of deposition, e.g. ballistic or more general forced deposition of analyte particles at interfaces or in compartments.

ii. The compartments are treated chemically and/or physically to amplify the presence of at least a predetermined threshold number $m_{tr_i}$ or predetermined threshold concentration $c_{tr_i}$ of analyte particles in compartment (i) to a measurable signal. Most generally, the threshold number or concentration of analyte particles may depend on the properties $(\Gamma_i)$ of compartment (i) as set out above under item i) or on the properties $(T_i)$ of the amplification treatment of compartment (i), in case the treatment is varied between the compartments. The predetermined threshold number $m_{tr_i}$ or predetermined threshold concentration $c_{tr_i}$ of analyte particles may also differ for part or all of the compartments (i). For example, these threshold values $m_{tr_i}$ and $c_{tr_i}$ may be functions of the properties $(\Gamma_i)$ of compartment (i) as set out above under item i) and/or of the properties $(T_i)$ of the amplification treatment in compartment (i). It may be advantageous to vary the properties $(\Gamma_i)$ of compartment (i) and/or the properties $(T_i)$ of the amplification treatment in compartment (i), as the dynamic range of the inventive assay can furthermore be adjusted, preferably broadened.

iii. Two or more of the number (N) compartments are monitored for and assigned a "digital" value in accordance with step a) of the inventive method, i.e. in case compartment (i) comprises the predetermined threshold number $m_{tr_i}$ or predetermined threshold concentration $c_{tr_i}$ of analyte particles the first value $(k_i)$, a "positive" value, e.g. 1, is assigned to compartment (i). In case compartment (i) comprises less than the predetermined threshold number $m_{tr_i}$ or predetermined threshold concentration $c_{tr_i}$ of analyte particles, the second value $(k_i)$, a "negative" value, e.g. 0, is assigned to this compartment (i). Any suitable method can be used for measuring and assigning the "digital" value ("positive" or "negative") to the compartments. The compartments can comprise the same volume $(v_i)$ and dilution factor $(d_i)$ or part or all of them can differ by volume $(v_i)$ and/or dilution factor $(d_i)$. With respect to the multivolume/multidilution approaches to be also applicable with respect to the present invention the disclosure thereof in Shen, F.; Sun, B.; Kreutz, J. E.; Davydova, E. K.; Du, W.; Reddy P. L.; Joseph, L. J.; Ismagilov, R. F., "Multiplexed Quantification of Nucleic Acids with Large Dynamic Range Using Multivolume Digital RT-PCR on a Rotational SlipChip Tested with HIV and Hepatitis C Viral Load", J. Am. Chem. Soc., Article ASAP (X 2011); in WO 2012/100198 A2 and in PCT/EP2012/004792 is incorporated herein by reference.

iv. In addition for at least two or more of the number (N) compartments the "analogue" value $(\tau_i)$ is determined respectively in accordance with step b) of the inventive method, wherein at least for one compartment thereof the value $(k_i)$ is also determined in accordance with step a) of the inventive method. Preferably the "analogue" values are measured with finite resolution. More preferably the "analogue" values $(\tau_i)$ depend on the number of analyte particles in the compartment (i) and comprise univocally and monotonically increasing functions of the number of analyte particles. The term "comprise" means in this context that in practical realizations the "analogue" value may comprise a term that is an univocal function of the number of analyte particles and a stochastic term. The functional dependence may be of any suitable type, e.g. the amplitude of the values may be linear in the concentration of analyte particles, square in the concentration of analyte particles, or exponential in the number of analyte particles, or any other kind that satisfies the requirement. In the context of the present invention it is assumed that obtaining an "analogue" value comprises within itself the information that the compartment (i) contains at least the threshold number or concentration (amount) of analyte particles required to obtain the "positive" digital first value $(k_i)$. This assumption follows from the fact that in general, "analogue" recording of signals is more demanding and in praxis realizations should not be more sensitive than the digital recording. If it were more sensitive, it would be chosen for the digital recordings. Nonetheless, with minor modifications that should be clear to those skilled in the art, the case when assigning an "analogue" value does not imply a "positive" digital first value, can also be treated with the current invention v. The estimate of concentration of analyte particles E(C) is then inventively determined as a function of part or all "digital" values $(k_i)$ assigned in step a) and part or all "analogue" values $(\tau_i)$ assigned in step b). In accordance with the present invention the "digital" values $(k_i)$ assigned in step a) and the "analogue" values $(\tau_i)$ assigned in step b) of the inventive method can generally be transformed by any known and suitable statistical algorithms, preferably by use of the Bayes theorem into the estimate of concentration.

vi. For the compartments, where an "analogue" value $(\tau_i)$ is determined respectively for the compartments, preferably the density of probability $\rho_i(k_i,\tau_i|C)$ is constructed on the basis of the properties $(\Gamma_i)$ of compartment (i), of the treatment $(T_i)$ of compartment (i) (e.g. amplification), and at least part or all of the "analogue" values $(\tau_i)$.

a. In a preferred example, the density of probability of the determinable concentration of analyte particles is preferably determinable by use of the function $\rho_i(k_i, \tau_i|C) = \rho_i(f(\{\tau_i\}), \Gamma_i, T_i, C)$ with properties ($\Gamma_i$) of compartment (i) and amplification treatments ($T_i$) of compartment (i).

b. In a more preferred, non limiting example, the function of analogue values $f(\tau_i, \tau_{R_i})$ preferably depends on a pair of values of the analogue value ($\tau_i$) from compartment (i) and a predetermined reference compartment ($R_i$).

c. In a furthermore preferred, non limiting example, with respect to the function the function $f(\tau_i, \tau_{R_i})$ the reference compartment (R) is preferably the same for all compartments (i).

d. In an even more preferred and non-limiting example, the reference compartment (R) is predetermined to be the compartment (i) characterized by the smallest expected number of analyte particles of compartments containing at least a threshold number ($m_{tr_i}$) or concentration ($c_{tr_i}$) of analyte particles.

vii. The "positive" digital first values ($k_i$) assigned to those compartments, where no "analogue" value ($\tau_i$) is determined for, are preferably translated into a density of probability $\rho_i(k_i|C)$ or $\rho_i(k_i|M)$ (of concentration or number of analyte particles in the sample) that is a function of the probability distribution $p_i(m_i)$, of the number of analyte particles and of the properties ($\Gamma_i$) of compartment (i), e.g. of the volume of the compartment and the dilution factor of the compartment and possibly other factors (such as e.g. surface to volume ratio, the amplitude of force used to attract analyte particles, chemical affinity etc). For example, for a Poissonian distribution of analyte particles in compartments, $\rho_i(k_i=\text{positive}|C) = 1 - e^{-Cd_i v_i} \sum_{j=1}^{m_{tr}-1} [(Cd_i v_i)^j/j!]$.

viii. The "negative" digital second values ($k_i$) assigned to those compartments, where no "analogue" value ($\tau_i$) is determined for, are preferably translated into a density of probability $\rho_i(M)$ or $\rho_i(C)$ (of concentration or number of analyte particles in the sample) that is a function of the distribution $p_i(m_i)$, of the number of analyte particles and of the properties ($\Gamma_i$) of compartment (i), e.g. of the volume of the compartment and the dilution factor of the compartment and possibly other factors (such as e.g. surface to volume ratio, the amplitude of force used to attract analyte particles, chemical affinity etc). For example, for a Poissonian distribution of analyte particles in compartments, $\rho_i(k_i=\text{negative}|C) = e^{-Cd_i v_i} \sum_{j=0}^{m_{tr}-1} [(Cd_i v_i)^j/j!]$.

ix. In a preferred embodiment of the present inventive method the product $\Psi(\{k_i\},\{\tau_i\}|C)$ of the densities of probability $\Psi(\{k_i\},\{\tau_i\}|C) = \Pi_i \rho_i(k_i, \tau_i|C)$ provides the result of the inventive method in the form of a probability density of obtaining the measured result of the assay as a function of the unknown concentration of the analyte particles. To determine the concentration (or determine the initial number) of analyte particles in the sample, the probability distribution $\Psi(\{k_i\},\{\tau_i\}|C)$ should be inverted using known mathematical algorithms (i.e. Bayes theorem) to find a probability distribution of the concentration $P(C|\{k_i\},\{\tau_i\})$ that caused a measured outcome of the assay.

x. Preferably the product $P(C|\{k_i\},\{\tau_i\})$ (or $P(M|\{k_i\},\{\tau_i\})$) can be conveniently simplified to the estimate of concentration of analyte particles in the predetermined sample volume $E(C) = \int_0^\infty P(C|\{k_i\},\{\tau_i\})dC$ (or $E(M) = \int_0^\infty P(M|\{k_i\},\{\tau_i\})dM$) and the standard deviation of the distribution $\sigma(C) = \sqrt{E(C^2) - E^2(C)}/E(C)$ (or $\sigma(M) = \sqrt{E(M^2) - E^2(M)}/E(M)$).

xi. Optionally for a predetermined set up of the inventive method, i.e. the number and character of the compartments and the method of partitioning the sample volume, it may be convenient to tabularize the relation between $E(C)$ and $\sigma(C)$ (or $E(M)$ and $\sigma(M)$) and the set of values (or simply the number of positive values). Nonetheless, such simplified inventive methods of analysis are always underlined by the calculations described in points i-ix.

xii. Optionally, either the probability density function $P(C|\{k_i\},\{\tau_i\})$ (or $P(M|\{k_i\},\{\tau_i\})$) calculated in point ix. or the estimate of concentration of analyte particles in the predetermined sample volume $E(C)$ or $E(M)$ calculated in point x. may be corrected using a calibration correction function. The suitable calibration correction function may be determined experimentally, using standard samples with concentrations of analyte particles within the dynamic range of the test. The calibration correction can also be computed numerically based on the dependence of the estimate $E(C)$ of the concentration of analyte particles in the sample and the actual concentration of particles C randomly distributed in compartments, or based on the dependence of the estimate $E(M)$ of the number of particles in the sample and the actual number of particles M randomly distributed in compartments. Having computed the calibration correction $f_{corr}(C)$, the corrected estimate of the number of particles is determinable, preferably determined with the formula $E_{corr}(C) = E(C) \cdot f_{corr}(C)$. For example, for a quantitation assay comprising N=380 compartments with modulation factors $\{d_i v_i\}$ given by a geometric sequence with common ratio x=0.954 and the first element $d_i v_i$=5.27495 µL, provided the amplification factor q=2 the correction is $f_{corr}(C)$=0.7042.

The present invention can also be used if the threshold number of analyte particles ($m_{tr_i}$) or threshold concentration of analyte particles ($c_{tr_i}$) in compartment (i) is given by a predetermined probability distribution $p_i(m_i)$ of the number ($m_i$) of analyte particles that were distributed to the compartment (i). In such a case the predetermined probability distribution should be used in the calculation of the functions $\rho_i$ described in points vii. and viii. via a convolution that will be known to those skilled in the art.

In the following discussion the application of the inventive method to the Real-Time PCR assays is in focus, although the inventive method can also be applied to various other assays. In contrast to the present invention, the digital assays of the prior art provide only binary information, the "digital" yes/no answer whether there was a finite threshold amount of analyte particles (threshold concentration) present in the predetermined sample volume reflected by a "positive" value, or the opposite case—reflected by a 'negative' value. The information of the digital assay of the prior art could be gained by a single measurement from each test volume after a large number of cycles of PCR has been performed (i.e. an end-point signal). In accordance with the present invention the inventive method requires measurements and determinations (assignments) of "analogue" values from at least part or all of the sample compartments.

In accordance with the "digital" measurement of step a) of the inventive method it can be determined whether a predetermined compartment (i), characterized by a volume ($v_i$) and dilution factor ($d_i$), contained initially at least a threshold number (or threshold concentration) of analyte particles, then the "positive" first value ($k_i$) is assigned to compartment (i) which confirms the hypothesis or otherwise a "negative" second value ($k_i$) is assigned to compartment (i). Each of these readouts conveys a probabilistic information about the initial concentration of analyte particles in the sample. For example, under the assumption that the number of analyte particles in the partition is predetermined by a Poissonian distribution $p_i(m_i)=e^{-Cd_iv_i}(Cd_iv_i)^{m_i}/m_i!$, the positive signal can be translated into a density of probability that a given initial concentration of analyte particles in the sample has caused the positive recording from the partition: $p_i(k_i=\text{positive}|C)=1-e^{-Cd_iv_i}\Sigma_{j=0}^{m_{tr}-1}[(Cd_iv_i)^j/j!]$. For example, for $m_{tr}=1$, $p_i(k_i=\text{positive}|C)=1-e^{-Cd_iv_i}$. Similarly, the negative signal can be translated into $p_i(k_i=\text{negative}|C)=e^{-Cd_iv_i}\Sigma_{j=0}^{m_{tr}-1}[(Cd_iv_i)^j/j!]$. For example, for $m_{tr}=1$, $p_i(k_i=\text{negative}|C)=e^{-Cd_iv_i}$. The resulting sigmoidal probability functions are centered (i.e. has the value of ½) at a concentration determined by the characteristics of the compartment only, i.e. in the example, at $C^*=\ln(2)/(v_id_i)$ (see FIGS. 1a), 1b) and 1c) as set out below in the detailed description of the drawings).

The result of the whole digital measurement in step a) of the inventive method (i.e. of the readouts from part or all the compartments) is preferably determinable by the product of all the probability densities obtained from the individual compartments (i): $\Psi(\{k_i\}|C)=\Pi_{i=0}^{N-1}p_i(k_i|C)$. FIG. 1c) shows an example of $(\Psi(\{k_i\}|C))$ calculated for "digital" values ($k_i$) from two identical compartments.

In general, since the sigmoidal contributions from the compartments (i) are centered on the concentrations that depend solely on the properties of the compartment and do not depend on the actual concentration of analyte particles in the sample, many values ($k_i$) contribute little to the result of the inventive method. In particular, the values ($k_i$) from compartments that contain high expected number of analyte particles ($m_i \gg 1$), or very small expected number of analyte particles ($m_i \ll 1$), do not contribute much to the result of a solely digital method. This is because in the range of concentrations similar to the actual concentration of the analyte particles in the sample, these functions are closely equal to unity and almost constant (see FIGS. 2a) and 2b) as set out below in the detailed description of the drawings).

In accordance with the present invention the use of the "analogue" measurement of step b) of the inventive method further improves the precision of the inventive assay. According to the inventive method, the information from the digital recordings of step a) can be used to calibrate the information of the "analogue" values ($\tau_i$) determined in step b). This in turn can increase the informational content of the "positive" values ($k_i$) from the compartments that were also inspected for the analogue measurement. In the exemplary embodiment of the inventive method comprising an application to a PCR amplification of the presence of nucleic acids, at least part of the compartments is inspected for a time or cycle interval ($\tau_i$) at which the intensity of fluorescence of compartment (i) exceeds the predetermined threshold number $m_{tr_j}$ or predetermined threshold concentration $c_{tr_j}$ of analyte particles. According to the prior art (i.e. the Real-Time PCR procedures), the recording of the intervals ($\tau_i$) and ($\tau_j$) for two separate compartments, allows to estimate the ratio of initial numbers of analyte particles in them as: $m_i/m_j=q^{\tau_j-\tau_i}$, where (q) is the amplification factor in a Real-Time PCR procedure, given by the ratio of the number (or concentration) of amplicons in two consecutive cycles of the procedure.

The dependence between the number of analyte particles and the analogue value ($\tau_i$) is not limited to an exponential function. The inventive method described herein improves the precision of the assay for any non-trivial functional dependence between the number of analyte particles and the analogue value ($\tau_i$) provided that this relationship is a priori known. For example, if the value of analogue value ($\tau_i$) is determined directly as the level of fluorescence from the analyte particle in the compartment (i), it is linearly proportional to the number these particles. Thus, the estimated ratio of initial numbers of analyte particles in two compartments (i) and (j) is equal to: $m_i/m_j=\tau_i/\tau_j$. Other measurements that provide other functional relationships between the number of particles of the analyte particle and the analogue value are known to those skilled in the art and may be applied if appropriate.

According to the present invention, this information can be used to improve the informational content contributed from the "positive" digital first values ($k_i$) of compartments (i). In a non-limiting, preferred, example, from the set of compartments that are measured in accordance with step b) of the inventive method, preferably the value ($\tau_{R_i}$) of a reference compartment ($R_i$) is determined, more preferably the reference compartment ($R_i$) is expected to contain initially the smallest number of analyte particles, more preferably the reference compartment (R) is the same for all compartments (i).

Based on the information that the reference compartment ($R_i$) generally contains at least a threshold number or concentration of analyte particles, and that the values $\{\tau_i\}$ are determined based on the measurements in step b) of the inventive method, it can inventively be determined that compartment (i) contains at least the number ($m_i$) analyte particles, wherein ($m_i$) is preferably determined by the function $$m_i = m_{R_i} q^{\tau_{R_i}-\tau_i}.$$

This inventive method is advantageous, as it shifts the sigmoidal function $p_i(k_i=\text{positive}|C)=1-e^{-Cd_iv_i}$ to be centered closer to the actual concentration in the sample (see FIGS. 2a) and 2b) as set out below in the detailed description of the drawings). This procedure according to the present invention surprisingly allows to improve the precision and accuracy of the result of the assay: $\Psi(\{k_i\}|C)=\Pi_{i=0}^{N-1}p_i(k_i|C)$.

The current invention is not limited to the PCR methods but can be applied to a wide range of assays in which it is possible to combine the digital and analogue information from separate compartments. For example, the dependence between the number of analyte particles and the analogue value is not limited to an exponential function. The inventive method described hereinbefore improves the precision of the assay for any non-trivial functional dependence between the number of analyte particle and the analogue value provided that this relationship is a priori known or approximately known. For example, if the analogue value is linearly proportional to the number or concentration of these analyte particles and the number or concentration of analyte particles may increase at a steady rate during the amplification process, then the estimated ratio of initial numbers of analyte particles in two compartments (i) and (j) will be equal to: $m_i/m_j=\tau_i/\tau_j$. Other measurements that provide other functional relationships between the number of analyte particles and the analogue value are known to those skilled in the art.

The inventive method described herein can use any type of analogue information that comprises an univocal relationship of its magnitude with the number or concentration of particles of analyte particles in a compartment.

Furthermore, the use of "analogue" measurement of step b) of the inventive method allows to determine the amplification factor (q), i.e. the average of the ratio of the numbers of analyte particles in the test volume after two subsequent cycles or time intervals, if the amplification factor (q) is not a priori known. The advantage of the present invention is, that the amplification factor (q) can specifically be determined for the current sample and/or current substrate and/or current apparatus, and each measurement can be treated separately.

The amplification factor (q) can preferably be determined/calculated as follows:
  i. for a known sequence of $\{d_i v_i\}$, the "analogue" values $\{\tau_i\}$ is determined,
  ii. observing threshold level of fluorescence is a sign, that the current number of analyte particles in the compartments is equal to some constant value (possibly unknown), hence the inventors postulate that $m_{obs} = m_i q^{\tau_i}$, where $m_{obs}$ is the threshold number and $m_i$ is the initial number of analyte particles
  iii. the expected value of $E(m_i)$ is equal $d_i v_i C$, where C is constant (it is the real value of concentration) and unknown
  iv. then, from the measurement of $\{\tau_i\}$ and a priori knowledge of $\{d_i v_i\}$, one can plot $\tau_i = f(\ln(d_i v_i))$
  v. the gradient of the linear fit to this data is equal to $\alpha = f(q) = 1/\ln(q)$, hence $q = e^{-1/\alpha}$.

In accordance with the present invention the required constant precision given by the maximum relative standard deviation ($\alpha_{max}$) of the estimate of concentration and the required dynamic range $\Omega = C^+/C^-$ can be adjusted as described below.

In a non-limiting example of the use of the inventive method, for all number (N) compartments both the digital and the analogue values are determined in accordance with steps a) and b) of the inventive method. Accordingly, preferably a set of compartments is built with the products of volume and dilution $\{d_i v_i\}$ creating a geometrical sequence with common ratio x preferably determinable by:

$$x = \alpha \cdot \sigma_{max}^2 + \beta \cdot \sigma_{max} + \gamma,$$

where $\alpha$, $\beta$ and $\gamma$ are constants and preferably $\alpha = 0.5009$, $\beta = -1.5798$ and $\gamma = 1.0887$.

The first (preferably the largest) element $d_0 v_0$ of this sequence is preferably determinable by:

$$d_0 v_0 = \ln 2 \cdot x^{-\Delta N/2}\left(\frac{1}{C^-}\right),$$

where $\Delta N$ is preferably determinable by:

$$\Delta N = \delta \cdot \sigma_{max}^{-2} + \in \cdot \sigma_{max}^{-1} + \varphi,$$

where $\delta$, $\in$ and $\varphi$ are constants, preferably $\delta = 0.7343$, $\in = 4.849$ and $\varphi = 1.9601$.

The number of elements of this sequence N is preferably determinable by $$N = \Delta N + \log_x\left(\frac{C^-}{C^+}\right).$$

In a more efficient, non limiting example, the set of compartments $\{d_i v_i\}$ is preferably determinable by the following close approximations:

$$x = \alpha \cdot \sigma_{max}^5 + \beta \cdot \sigma_{max}^4 + \gamma \cdot \sigma_{max}^2 + \delta \cdot \sigma_{max}^2 + \in \cdot \sigma_{max} + \varphi,$$

where $\alpha$, $\beta$, $\gamma$, $\delta$, $\in$ and $\varphi$ are constants and preferably $\alpha = 5.4551$, $\beta = -15.606$, $\gamma = 16.333$, $\delta = -7.0673$, $\in = -0.1055$ and $\varphi = 1$.

The first (preferably the biggest) element $d_0 v_0$ of this sequence is preferably determinable by:

$$d_0 v_0 = \ln 2 \cdot x^{-\Delta N/2}\left(\frac{1}{C^-}\right),$$

where $\Delta N$ is preferably determinable by:

$$\Delta N = \lambda \cdot \sigma_{max}^{-2} + \nu \cdot \sigma_{max}^{-1} + \xi,$$

where $\lambda$, $\nu$ and $\xi$ are constants, preferably $\lambda = 0.7343$, $\nu = 4.849$ and $\xi = 1.9601$.

The number of elements of this sequence N is preferably determinable by $$N = \Delta N + \log_x\left(\frac{C^-}{C^+}\right).$$

For some analytical applications, the required precision of the estimation of concentration may vary for different concentration ranges. Hence, the inventive method can be tuned (adjusted) in order to provide different precision ($\sigma_{max}$) by changing the common ratio (x) of the geometric series of volume and dilution product $d_i v_i$. Preferably, the interval $(C^-, C^+)$ can be divided into j subintervals $(C_n^-, C_n^+)$, preferably disjoint ones, in each subinterval the set of values $d_i v_i$ is preferably a decreasing geometric series with quotient $x_n$, whereas:

For $\sigma_{max_n} < \sigma_{max_{n-1}}$:

$$x_n = \alpha_n \cdot \sigma_n^5 + \beta_n \cdot \sigma_n^4 + \gamma_n \cdot \sigma_n^2 + \delta_n \cdot \sigma_n^2 + \in_n \cdot \sigma_n + \varphi_n,$$

where $\alpha$, $\beta$, $\gamma$, $\delta$, $\in$ and $\varphi$ are constants and preferably $\alpha = 5.4551$, $\beta = -15.606$, $\gamma = 16.333$, $\delta = -7.0673$, $\in = -0.1055$ and $\varphi = 1$ $$\Delta N_n = \lambda \cdot \sigma_{max_n}^{-2} + \nu \cdot \sigma_{max_n}^{-1} + \xi,$$

where x is the common ratio of the sequence and $\delta$ and $\in$ are constants, preferably $\lambda = 0.7343$, $\nu = 4.849$ and $\xi = 1.9601$ $$N_n = \Delta N_n + \log_{x_n}\left(\frac{C_n^-}{C_n^+}\right)$$

$$d_{n_0} v_{n_0} = \ln 2 \cdot x_n^{-\Delta N_n/2}\left(\frac{1}{C_n^-}\right)$$

For $\sigma_{max_n} > \sigma_{max_{n-1}}$ $$x_n = \alpha \cdot \sigma_{max_n}^5 + \beta \cdot \sigma_{max_n}^4 + \gamma \cdot \sigma_n^2 + \delta \cdot \sigma_{max_n}^2 + \varepsilon \cdot \sigma_{max_n} + \varphi,$$

where $\alpha$, $\beta$, $\gamma$, $\delta$, $\in$ and $\varphi$ are constants and preferably $\alpha = 5.4551$, $\beta = -15.606$, $\gamma = 16.333$, $\delta = -7.0673$, $\in = -0.1055$ and $\varphi = 1$ $$\Delta N_n = \lambda \cdot \sigma_{max_n}^{-2} + \nu \cdot \sigma_{max_n}^{-1} + \xi,$$

where $\lambda$, $\nu$ and $\xi$ are constants, preferably $\lambda = 0.7343$, $\nu = 4.849$ and $\xi = 1.9601$ $$N_n = 0.5\Delta N_n + 0.5\Delta N_{n-1} + \log_{x_n}\left(\frac{C_n^-}{C_n^+}\right)$$

$$d_{n_0}v_{n_0} = \ln 2 \cdot x_{n-1}^{-\Delta N_n-1/2}\left(\frac{1}{C_n^-}\right)$$

Where $C^-$ means the lower limit of the interval for the determination of the unknown concentration C, $C^-$ means the upper limit of the interval for the determination of the unknown concentration C, $C_n^-$ means the lower limit of the subinterval with the number n, $C_n^+$ means the upper limit of the subinterval with the number n, $\sigma_{max_n}$ means the maximum permitted standard deviation of the estimate E(C) of the unknown concentration C of analyte particles in the sample in the subinterval $(C_n^-\text{-}C_n^+)$, n is the subinterval number, running over integers from 1 to j, and i is the compartment number, running over integers from 0 to N−1.

In the context of the present invention the logarithmic distance between the compartments (i) is generally much smaller than the standard deviation of the estimate of concentration C, formally $(x^{-1}-1) \ll \sigma_{max}$. Thus, one may expect that the high precision results more from the number of compartments than from the fine gradation of their volumes. As generation of such a fine gradation (for e.g. x=0.99) may be technically challenging, it is reasonable to use inventive methods with larger gradations (i.e. smaller values of x) with copies of each compartment, similarity to the multi-volume approach of Ismagilov et al. (F. Shen, R. F. Ismagilov et al., JACS 2011 133: 17705-17712), wherein the teaching thereof in the context of compartment building, which can also be used with respect to the inventive method, is incorporated herein by reference. For example, each $d_i v_i$ partition can be multiplied $N'_i$ times, increasing the number of compartments in the inventive method up to $N_{tot} = \Sigma_{i=0}^{N-1} N'_i$. Then, the digital binary values $k_{i,j}$ from the compartments (indexed j within each set i) can be represented by a set of real numbers $K_i$ proportional to the number of positive compartments belonging to the i-th family $d_i v_i$.

If the multiplicity of each family is constant, i.e. $V_{i=0}^{N-1} N'_i = N'$, standard deviation of the estimate E(C) is proportional to $1/\sqrt{N'}$. Hence, for any predetermined required $\sigma_{max}$ the value of x is preferably determinably by:

$$x_n = \alpha \cdot (\sigma_{max}\sqrt{N})^5 + \beta \cdot (\sigma_{max}\sqrt{N})^4 + \gamma \cdot (\sigma_{max}\sqrt{N})^3 + \delta \cdot (\sigma_{max}\sqrt{N})^2 + \in \cdot (\sigma_{max}\sqrt{N}) + \varphi,$$

where $\alpha, \beta, \gamma, \delta, \in$ and $\varphi$ are constants and preferably $\alpha=5.4551$, $\beta=-15.606$, $\gamma=16.333$, $\delta=-7.0673$, $\in=-0.1055$ and $\varphi=1$.

Alternatively, if, depending on the capabilities of laboratory equipment, it may be advantageous to prefer a predetermined value of x: $N'(x, \sigma_{max})$. With $\Delta N$, N and $v_0$ preferably calculated in the same routine as in the case without families of compartments. This allows to freely exchange the value of the multiplier x into the number of copies of compartments N' while keeping the same required standard deviation of the estimate.

In accordance with an alternative inventive embodiment of the inventive method of the first aspect of the invention the partitioning of the sample can also be based on the analysis of the distribution of "analogue" values $(\tau_i)$. Their distribution is generally determined by the distribution of analyte particles in compartments (which can be Poisson distribution with parameter $\lambda = Cd_i v_i$). The relative standard deviation of this distribution is generally equal to $1/\sqrt{\lambda}$, hence it decreases with the increase of C (for known $d_i v_i$). Another component of the spread of values $(\tau_i)$ is the inaccuracy of the experimental set-up. This can be described by the Normal distribution with expected value 0 and standard deviation $\sigma_t$, which is constant and does not depend on C. The spread of values $(\tau_i)$ is therefore a statistical effect of these two distributions. If the inaccuracy of the experimental set-up (i.e. inaccuracy of analog measurement) is known, then the spread of values $(\tau_i)$ can be used to determine the initial concentration C of the analyte using known statistical and mathematical algorithms (i.e. Borel measure, statistical test $\chi^2$).

The inventors of the presented invention have noticed, that the distribution of analog values assigned to compartments depends on the initial concentration (C) of the analyte or the initial number of analyte particles (M) in the sample. The dependence roots in the distribution of particles of the analyte between N compartments. For example, under the assumption, that the number of molecules $\{m_i\}$ are distributed in N identical compartments $d_i v_i$ follows a Poisson distribution, the variance of this distribution is $\text{Var}(\{m_i\}) = \lambda = Cd_i v_i$. Hence, in a non-limiting example, if the ideal analogue value assigned to the i-th is equal to the number of PCR cycle after which the signal overcomes a threshold value, i.e. $\tau_i = \log_q m_{obs_i} - \log_q m_i$, the variance of the distribution of ideal analogue values assigned to compartments can be given as $\text{Var}(\{\tau_i\}) = [(\ln(q))^2 Cd_i v_i]^{-1}$. If the uncertainty of the measurement itself is given by a normal distribution with a known standard deviation $\sigma_t$, i.e. $N(0, \sigma_t)$, the distribution of the real measurements is a sum of these two distributions, and its variance is equal to $\text{Var}(\{\tau_i\}) = [(\ln(q))^2 Cd_i v_i]^{-1} + \sigma_t^2$, $\sigma_t = \text{const}$. Hence, on the basis of the spread of the analogue values assigned to compartments, it is possible to define an univocal function of the concentration C of the analyte. The hypothesis of the value of concentration may be calculated using known statistical methods, i.e. statistical test $\chi^2$, which can be also used to determine the minimal number of compartments needed to determine the concentration with a given precision at a given confidence level.

In accordance with the second aspect of the present invention an apparatus for use in determining a concentration of analyte particles in accordance with the inventive method is provided. All of the embodiments of the first aspect of the present invention can be combined independently from each other with respect to the second aspect of the invention.

The inventive apparatus enables amplification of the analyte particles, the measurement of the signals and assignment of "digital" first and second values $(k_i)$ in accordance with step a) of the inventive method, determination of "analogue" values $(\tau_i)$ in accordance with step b) of the inventive method as well as the determination of the estimate of concentration E(C) by suitable means in accordance with step c) of the inventive method. In a preferred embodiment the inventive apparatus preferably enables carrying out the determination of the number (N) of compartments and the determination of the modulation factor $(z_i)$ of the expected number of particles, by suitable means.

Suitable means for configuring the preferred apparatus have been disclosed with respect to the first aspect of the present invention and can be combined independently from each other with the aforementioned preferred apparatus of the present invention. Suitable means with respect to the determination of the estimate concentration E(C) are preferably computer with a memory device configured with executable instructions stored thereon, the instructions—when executed by a processor, cause the processor to determine the estimate of concentration E(C) in accordance with the present invention.

According to a third aspect of the present invention the use of the inventive method or the inventive apparatus is provided for a) reducing the total number (N) of compartments comprising the predetermined sample volume and/or
b) adjusting the precision and/or dynamic range and/or
c) eliminating the need of external calibration.

All the preferred embodiments of the first and second aspect of the present invention can independently from each other be combined with the embodiments of the third aspect of the present invention.

According to the fourth aspect of the present invention the inventive sample holder for use in an inventive method or with an inventive apparatus is provided, wherein the sample holder is inventively configured to a) comprising or consisting of a predetermined number (N) of compartments wherein the number (N) is smaller or equal to the value of the function $$N_{MAX} = B \cdot \ln\left(\frac{C^+}{C^-}\right) / \sigma_{MAX}^2$$

wherein (B) represents a real number being 1 or less, preferably 0.5 or less, more preferably 0.2 or less, further more preferably 0.1 or less wherein ($C^+$) represents a predetermined upper limit of the interval of concentration (C) to be estimated by the method, wherein ($C^-$) represents a predetermined lower limit of the interval of concentration (C) to be estimated by the method, herein ($\sigma_{MAX}$) represents a predetermined maximum allowable relative standard deviation of the estimate of concentration E(C) of analyte particles, wherein $C^- < C < C^+$, and b) wherein the (N) compartments are configured to comprising the predetermined sample volume with a predetermined modulation factor ($z_i$), wherein ($z_i$) is a function of volumes ($v_i$) and dilution factors ($d_i$) of the sample in at least part of or all of the (N) compartments so that at least part of or all of the two or more of the (N) compartments can comprise or consist of different sample volumes ($v_i$) and/or different dilution factors ($d_i$) of the sample, wherein (i) represents an index number of the (N) compartments represented by the integers 0 to N−1, and wherein ($v_i$) represents the volume and ($d_i$) represents the dilution factor of the sample in the compartment (i).

All the preferred embodiments of the first and second third aspect of the present invention can independently from each other be combined with the embodiments of the fourth aspect of the present invention.

Inventive sample holders can preferably comprise suitable test tubes, arrays of wells on a microarray, or a microfluidic chip, a microfluidic chip configured to generating droplets as well as other commercially available or otherwise generally known devices capable of holding discrete volumes and allowing amplification and measurement of respective signals.

The fifth aspect of the present invention relates to a kit comprising the inventive sample holder and one or more reagents suitable for amplifying at least part of analyte particles comprised in the compartments of the sample holder to a measurable signal and optionally one or more suitable diluents for determining a concentration of analyte particles, preferably for determining the concentration of analyte particles in accordance with the inventive method.

All the preferred embodiments of the first, second, third and fourth aspect of the present invention can independently from each other be combined with the embodiments of the fifth aspect of the present invention.

DETAILED DESCRIPTION OF THE FIGURES

In FIG. 1a) the graph shows that a single compartment (i) of volume $v_i$ and dilution d=1 gives a probability of amplification, i.e. of containing at least one analyte particle, that depends on the concentration of the analyte particle $p(k=1|C)=1-e^{-vC}$. The characteristic concentration $C^*$ yields $p(k=1|C^*)=0.5$. Recording of a signal and assigning the digital value ($k_i$) for compartment (i) ("positive" first digital value k=1; "negative" second digital value k=0) can be translated into a probabilistic information about the concentration of the analyte particle via the Bayesian formalism. The density of probability $\rho(C|k=1)$ has the same functional form as $p(k=1|C)$ and is normalized by an arbitrarily chosen upper bound $C_\infty$ of possible input concentrations. Similarly the probability of not-obtaining a signal from the compartment $p(k=0|C)=e^{-vC}$ can be translated into $\rho(C|k=0)$.

Figure 1B:
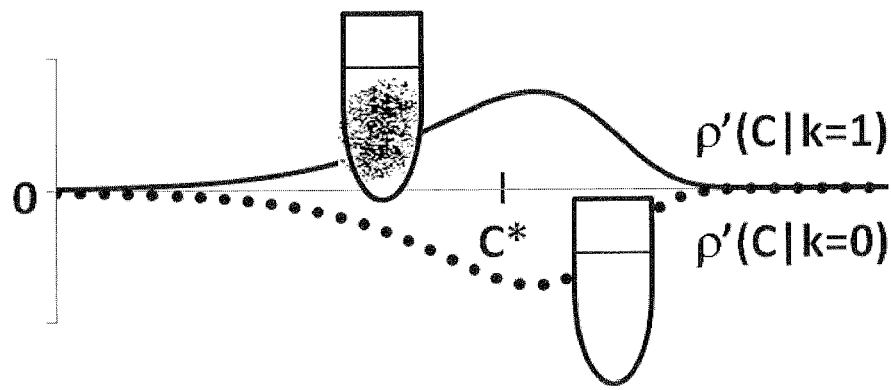
Figure 1C:
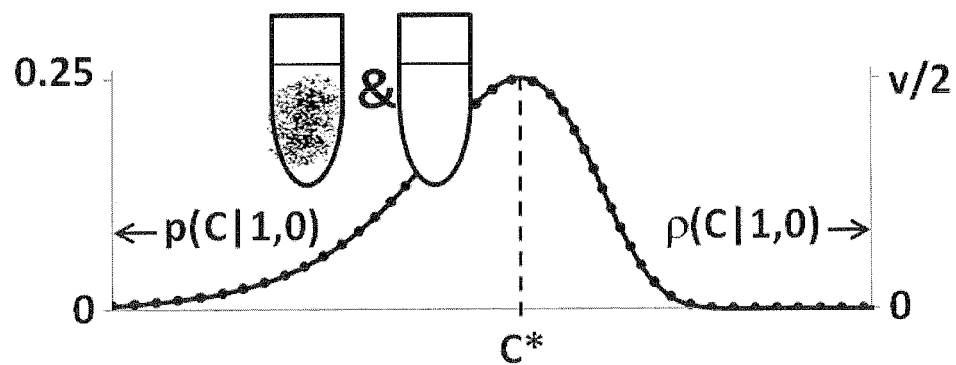

In FIG. 1b) the graph shows that both $\rho(C|k=1)$ and $\rho(C|k=0)$ change most rapidly around $C^*$ where $\rho'(C)=d\rho(C)/dC$ has an extremum. Thus the digital value ($k_i$) for compartment (i) provides most information about input concentrations similar to $C^*$.

In FIG. 1c) the graph shows that the information from each compartment can be combined. In the example, observation of the combination of the "positive" first digital value (k=1, i.e. threshold signal) and the "negative" second digital value (k=0; i.e. lack of signal) can be combined to yield $p(k_1=1, k_2=0|C)=e^{-vC}-e^{-2\ vC}$ and the corresponding density of probability of concentration.

Figure 2A:
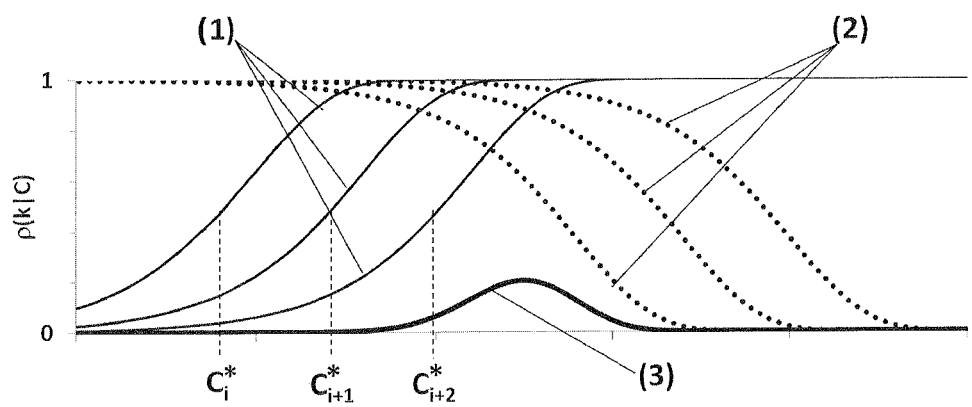
FIGS. 2a) and 2b): Graphs displaying the probabilistic information about the concentration of analyte particles based on the digital measurement alone or based on the digital measurement in combination with the analogue measurement.

In FIG. 2a) the graph shows a set (assay) of compartments with geometrical sequence of modulation factor $d_iv_i$. Larger compartments (1) yield "positive" first digital values while the other (2) yield "negative" second digital values. Digital values from compartments can be used to determine the probability density function (3) of the concentration of the analyte particles that caused such state of the assay.

Figure 2B:
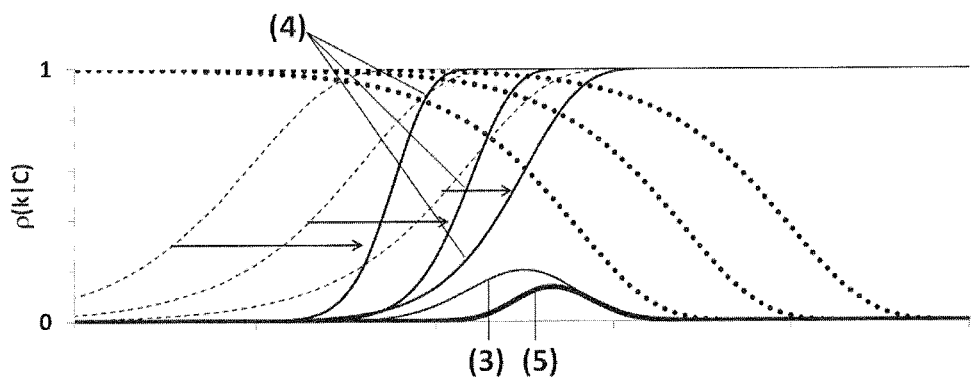

In FIG. 2b) the graph shows that if the digital measurement of step a) of the inventive method is accompanied with the analogue measurement in accordance with step b) of the inventive method, sigmoidal functions of probability for positive compartments can be shifted (4) towards the real value of concentration and new probability density function of concentration can be calculated (5). This new probability density function of concentration is narrower than the function based solely on digital measurement, and therefore provides higher precision (lower relative standard deviation) of the estimate of concentration.

Figure 3A:
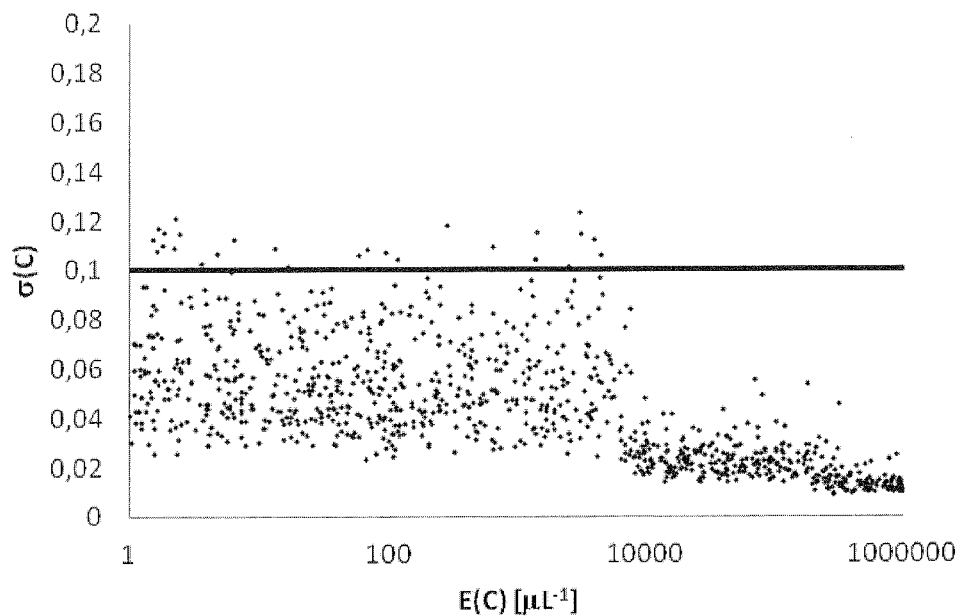
FIGS. 3a) and 3b): Graphs displaying the relative standard deviations of the estimate of concentration and the estimate of concentration determined via a Monte-Carlo simulation of the assays designed and executed according to the inventive method.

In FIG. 3a) the graph shows a distribution of values of relative standard deviation, which determines the precision, for an inventive quantitation assay designed to determine concentration of the analyte particle with a relative standard deviation less than $\sigma_{max}=10\%$ in the concentration range from $C^-=1$ mL$^{-1}$ to $C^+=10^6$ mL$^{-1}$, i.e., $C^+/C^-=10^6$. According to the inventive method the assay comprises N=380 compartments with modulation factors $\{d_iv_i\}$ given by a geometric sequence with common ratio x=0.954 and first element $d_0v_0=5.27495$ mL. The distribution was determined on the basis of 1000 Monte Carlo trials.

Figure 3B:
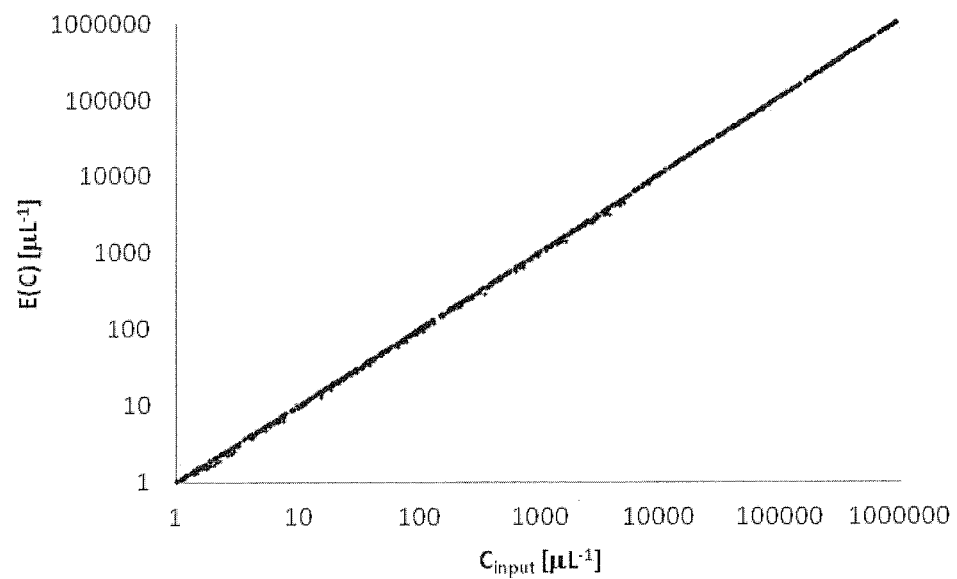

In FIG. 3b) the graph shows the relation between the corrected estimate of the concentration of the analyte particle and the real value of the concentration of the analyte particle.

Figure 4A:
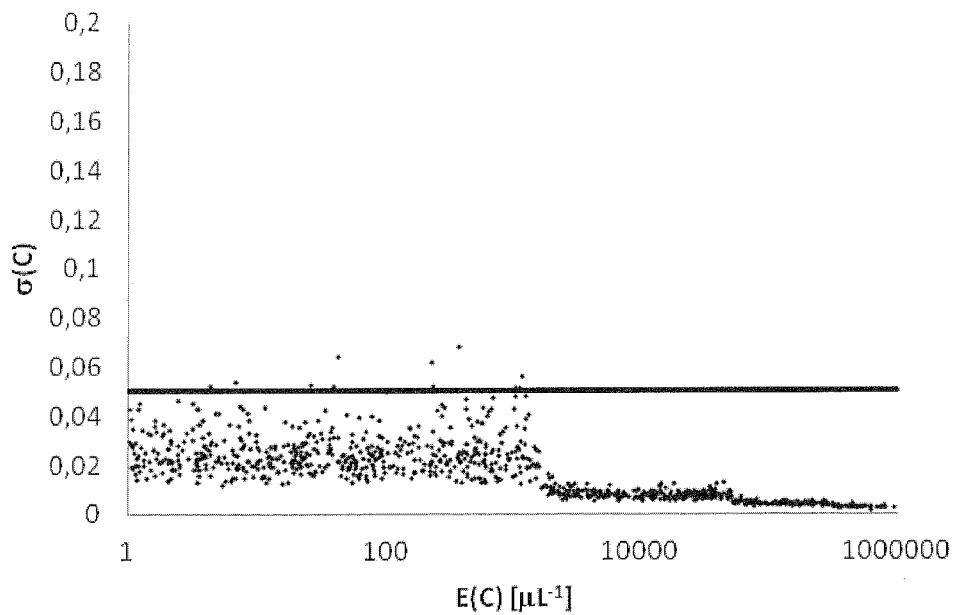
FIGS. 4a) and 4b): Graphs displaying the relative standard deviations of the estimate of concentration and the estimate of concentration determined via a Monte-Carlo simulation of the assays designed and executed according to the inventive method.

In FIG. 4a) the graph shows a distribution of values of relative standard deviation, which determines the precision, for an inventive quantitation assay designed to determine concentration of the analyte with a relative standard deviation less than $\sigma_{max}=5\%$ in the concentration range from $C^-=1$ mL$^{-1}$ to $C^+=10^6$ mL$^{-1}$, i.e., $C^+/C^-=10^6$. According to the inventive method the assay comprises N=1430 compartments divided into 143 sets with modulation factors $\{d_iv_i\}$ given by a geometric sequence with common ratio x=0.866 and the first element $d_0v_0=20.21$ µL. Each set comprised 10 identical compartments. The distribution was determined on the basis of 1000 Monte Carlo trials.

Figure 4B:
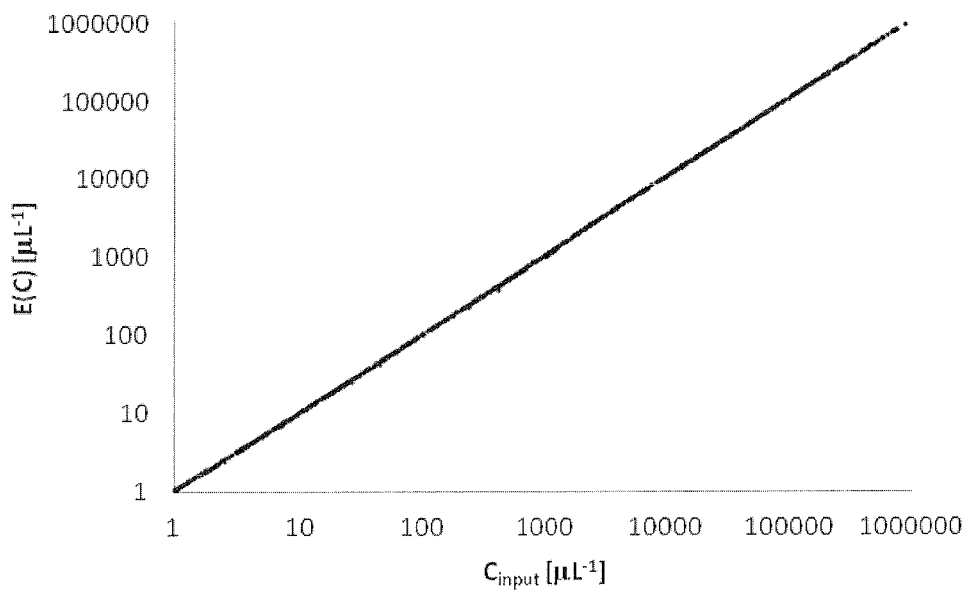

In FIG. 4b) The relation between the corrected estimate of the concentration of the analyte particle and the real value of the concentration of the analyte particle.

EXAMPLES

Executive Example 1

For the inventive quantification method we used the pJET1.2 plasmid with fragment of LepA gene cloned from *Mycobacterium Smegmatis*.

Real-Time PCR was performed in a volume of 10 µL, consisting of 2.5 µL of diluted plasmid DNA, 125 nM of forward and reverse primers (F: tcttgccctctttctgcttc, R: gatcggctcgagaatcattgcg) and 5 µL of SensiFAST SYBR No-ROX mix (Bioline). A three-step amplification protocol was performed in 7500 Fast Real-Time System (Applied Biosystems); an initial denaturation was performed with one cycle at 95° C. for 10 min. Subsequently, target amplification involved 50 cycles of 15 s at 95° C., 25 s at 62° C. for annealing, then extension for 15 s at 72° C. After 50 amplification cycles, PCR products were evaluated for quality using melt curve analysis, which entailed 15 s at 95° C., 1 min at 70° C., 15 s at 95° C. and 1 min at 55° C.

In a preferred embodiment of the invention the inventive quantitation assay is designed for an above sample with a volume of 10 µL so as to offer the estimate of the concentration of DNA molecules in the said sample with a relative standard deviation less than $\sigma_{max}=20\%$ in the concentration range from $C^-=5$ mL$^{-1}$ to $C^+=5\cdot10^6$ mL$^{-1}$, i.e., $C^+/C^-=10^6$. The assay returns the concentration of the sample calculated with the use of independent random variables, thus, via scaling the estimate of concentration in the sample can be translated into the estimate of concentration in a reservoir. The required dynamic range is accomplished by dividing the sample into 9 subsets, each comprising 7 identical compartments with dilution ratios between subsets $C_i/C_{sample}=d_i=x^i$, where x=0.215. Using numerical algorithms presented in the description of the invention, the estimate $E(C_{sample})$ is calculated based on the conditional probability distribution $P(C_{sample}|\{k_i\},\{\tau_i\})$, where $\{k_i\}$ are digital values assigned to compartments (i) and $\{\tau_i\}$ are analogue values determined for compartments (i).

For any digital negative value $(k_i)$ the corresponding probability function was $\rho_i(k_i=\text{negative}|C)=e^{-Cd_iv_i}$. For all the compartments that yielded a positive digital value $(k_i)$, the analogue value $(\tau_i)$ was determined. The compartment with the largest value of $(\tau_i)$ and therefore the smallest number of analyte particles was chosen to be the reference compartment R. Hence, any positive compartment (i) contained at least the number $(m_{tr_i})$ analyte particles, wherein $(m_{tr_i})$ was determined by the function $$m_{tr_i} = m_{tr_R} q^{\tau_R-\tau_i},$$

$$m_{tr_R} = 1.$$

Therefore the corresponding probability function was $$\rho_i(k_i = \text{positive}|C) = 1 - e^{-Cd_iv_i} \sum_{j=0}^{m_{min_i}-1} [(Cd_iv_i)^j/j!].$$

The result of the inventive assay was then: $\Psi(\{k_i\},\{\tau_i\}|C)=\Pi_{i=0}^{N-1}\rho_i(k_i,\tau_i|C)$, which was inverted using Bayes' theorem and then used to determine the expected value of initial concentration $E(C)$ and precision of this estimate $\sigma(C)$.

The analytical algorithm described above allows determining the initial concentration of the analyte particles, and the precision of this estimate. The results of 10 independent assays were: $E_1(C)=77.3$ µL$^{-1}$, $E_2(C)=81.9$ µL$^{-1}$, $E_3(C)=47.0$ µL$^{-1}$, $E_4(C)=80.5$ µL$^{-1}$, $E_5(C)=53.4$ µL$^{-1}$, $E_6(C)=53.0$ µL$^{-1}$, $E_7(C)=42.3$ µL$^{-1}$, $E_8(C)=59.5$ µL$^{-1}$, $E_9(C)=69.3$ µL$^{-1}$ and $E_{10}(C)=65.1$ µL$^{-1}$. The standard deviation of the distribution of this set of values is 20% (±1%) as expected according to the inventive method.

The individual features of the aforementioned executive example 1 may be separately combined with the individual preferred inventive embodiments of the general description.

Executive Example 2

The inventive method was used to design assays to verify their performance in terms of the precision of the estimate of the concentration of particles of analyte via Monte Carlo simulations. A quantitation assay was designed to determine the concentration of the analyte particles with a relative standard deviation less than $\sigma_{max}=10\%$ in the concentration range from $C^-=1$ µL$^{-1}$ to $C^+=10^9$ mL$^{-1}$, i.e., $C^+/C^-=10^6$. According to the inventive method the assay comprises N=380 compartments with modulation factors $\{d_iv_i\}$ given by a geometric sequence with common ratio x=0.954 and the first element $d_0v_0=5.27495$ µL. The assay returns the concentration of the sample calculated with the use of independent random variables, thus, via scaling the estimate of concentration in the sample can be translated into the estimate of concentration in a reservoir.

The input for the simulation was the distribution of analyte particles between compartments for a given concentration within the concentration range. We tested a set of 1000 different input concentrations of the analyte particles. For each such concentration we used numerical algorithms to distribute the analyte particles between the compartments randomly. The number of analyte particles in the compartment was a random variable with Poisson distribution with expected value $E(m_i)=Cd_iv_i$. For assigning digital values we set all the threshold values of the number of particles $m_{tr_i}=1$. Each compartment with the number of particles $m_i \geq m_{tr_i}$ was assigned with a positive digital value $k_i=1$. The compartments that had positive digital values were further assigned analogue values equal to the number of a cycle $(\tau_i=\log_q(m_{obs}/m_i)$, after which the number of amplicons overcome a given threshold value for detection $(m_{obs}=10^9)$ for a given amplification factor (q=2). Each compartment with the number of particles $m_i=0$ was assessed with a negative digital value $k_i=0$.

Using numerical algorithms presented in the description of the invention, the estimate $E(C_{sample})$ was further calculated based on the conditional probability distribution $P(C_{sample}|\{k_i\},\{\tau_i\})$, where $\{k_i\}$ are digital values and $\{\tau_i\}$ are analogue values assigned to the compartments. For any digital negative value $k_i$ the corresponding probability function was $\rho_i=e^{-Cd_iv_i}$. For all the compartments that yielded a positive digital value, the analogue value $\tau_i$ was determined. The compartment with the largest value of $\tau_i$ and therefore the smallest number of particles of the analyte was chosen to be the reference compartment R. Hence, any positive compartment (i) contained at least the number $(m_{min,\tau_i})$ analyte particles, wherein $(m_{min,\tau_i})$ was determined by the function $m_{min,\tau_i}=m_{min_R}q^{\tau_R-\tau_i}$, with $m_{min_R}=m_{min,k_R}=m_{tr}=1$. Therefore the corresponding probability function was $$\rho_i(k_i = \text{positive}|C) = 1 - e^{-Cd_iv_i} \sum_{j=0}^{m_{min,\tau_i}-1} [(Cd_iv_i)^j/j!].$$

The result of the assay was then: $\Psi(\{k_i\},\{\tau_i\}|C)=\Pi_{i=0}^{N-1}\rho_i(k_i,\tau_i|C)$, which was inverted using Bayes' theorem and used to determine the expected value of the initial concentration $E(C)$ and precision of this estimate $\sigma(C)$. Then, the estimate $E(C)$ of the initial concentration of the analyte was corrected using correction function $f_{corr}(C)=0.7042$.

In FIG. 3 (a) the distribution of the values of the precision $\sigma$ of the estimate $E(C)$ of the concentration, equal to the relative standard deviation of the estimate of concentration $E(C)$, based on 1000 trials is shown. For the vast majority of assessments, the relative standard deviation is smaller than 10% (solid line), as expected according to the inventive method. In FIG. 3b) the relation between the corrected estimate $E(C)$ of the concentration and the true value of concentration is plotted, showing a very good agreement between the calculated estimate and true value of concentration within the dynamic range of the assay.

The individual features of the aforementioned executive example 2 may be separately combined with the individual preferred inventive embodiments of the general description.

Executive Example 3

The inventive method was used to design assays and to verify their performance in terms of the precision of the estimate of the concentration of analyte particles via Monte Carlo simulations. An inventive quantitation assay was designed to determine the concentration of the analyte particle with a relative standard deviation less than $\sigma_{max}=5\%$ in the concentration range from $C^-=1$ $\mu L^{-1}$ to $C^+=10^9$ $mL^{-1}$, i.e., $C^+/C^-=10^6$. According to the inventive method the assay comprises N=1430 compartments divided into 143 sets with modulation factors $\{d_iv_i\}$ given by a geometric sequence with common ratio x=0.866 and the first element $d_0v_0=20.211$ $\mu L$. Each set comprised 10 identical compartments. The assay returns the concentration of the sample calculated with the use of independent random variables, thus, via scaling the estimate of concentration in the sample the estimate of concentration can be translated into estimate of concentration in a reservoir.

The input for the simulation was the distribution of analyte particles between compartments for a given concentration within the concentration range. We tested a set of 1000 different input concentrations of the analyte particles. For each such concentration we used numerical algorithms to distribute the analyte particles between the compartments randomly. The number of analyte particles in the compartment was a random variable with Poisson distribution with expected value $E(m_i)=Cd_iv_i$. For assigning digital values all the threshold values of the number of analyte particles were set to $m_{tr_i}=1$. Each compartment with the number of particles $m_i \geq m_{tr_i}$ was assigned with a positive digital value $k_i=1$. The compartments that had positive digital values were further assigned analogue values equal to the number of a cycle $(\tau_i=\log_q(m_{obs}/m_i)$, after which the number of amplicons overcome a given threshold value for detection $(m_{obs}=10^9)$ for a given amplification factor (q=2). Each compartment with the number of analyte particles $m_i=0$ was assessed with a negative digital value $k_i=0$.

Using numerical algorithms presented in the description of the invention disclosed hereinbefore, the estimate $E(C_{sample})$ was further calculated based on the conditional probability distribution $P(C_{sample}|\{k_i\},\{\tau_i\})$, where $\{k_i\}$ are digital values and $\{(i\}$ are analogue values assigned to the compartments. For any digital negative value $k_i$ the corresponding probability function was $\rho_i=e^{-Cd_iv_i}$. For all the compartments that yielded a positive digital value, the analogue value $\tau_i$ was determined. The compartment with the largest value of $\tau_i$ and therefore the smallest number of the analyte particles was chosen to be the reference compartment R. Hence, any positive compartment (i) contained at least the number $(m_{min,\tau_i})$ analyte particles, wherein $(m_{min,\tau_i})$ was determined by the function $m_{min,\tau_i}=m_{min_R}q^{\tau_R-\tau_i}$, with $m_{min_R}=m_{min,k_R}=m_{tr}=1$. Therefore the corresponding probability function was $$\rho_i(k_i = \text{positive}|C) = 1 - e^{-Cd_iv_i} \sum_{j=0}^{m_{min,\tau_i}-1} [(Cd_iv_i)^j/j!].$$

The result of the assay was then: $\Psi(\{k_i\},\{\tau_i\}|C)=\Pi_{i=0}^{N-1}\rho_i(k_i,\tau_i|C)$, which was inverted using Bayes' theorem and used to determine the expected value of the initial concentration $E(C)$ and precision of this estimate $\sigma(C)$. Then, the estimate $E(C)$ of the initial concentration of the analyte was corrected using correction function $f_{corr}(C)=0.7042$.

In FIG. 4a) the distribution of the values of the precision a of the estimate $E(C)$ of the concentration, equal to the relative standard deviation of the estimate of concentration $E(C)$, based on 1000 trials is shown. For the vast majority of assessments, the relative standard deviation is smaller than 5% (solid line), as expected according to the inventive method. In FIG. 4b) the relation between the corrected estimate $E(C)$ of the concentration and the true value of concentration is plotted, showing a very good agreement between the calculated estimate and true value of concentration within the dynamic range of the assay.

The individual features of the aforementioned executive example 3 may be separately combined with the individual preferred inventive embodiments of the general description.

The invention claimed is:
1. A method for determining an estimate of a concentration of analyte particles $E(C)$, wherein the analyte particles of a sample of predetermined volume are divided into a number (N) of two or more compartments, at least part of the analyte particles that are present in any of the (N) compartments provide for a measurable signal and the estimated concentration of analyte particles E(C) is a function of the measured signals, characterized in that the method comprises:
a) determining the number (N) of separate compartments, wherein the number (N) is smaller or equal to the value of the function:

$$N_{MAX} = A \cdot \ln\left(\frac{C^+}{C^-}\right)/\sigma^2_{MAX}$$

wherein (A) represents a real number equal to 6 or less, preferably 1 or less, more preferably 0.5 and even more preferably 0.2;
wherein ($C^+$) represents an upper limit of the interval of concentration (C) to be estimated by the method;
wherein ($C^-$) represents a lower limit of the interval of concentration (C) to be estimated by the method; and
wherein ($\sigma_{MAX}$) represents a maximum allowable relative standard deviation of the estimate of concentration (C) of analyte particles, wherein $C^-<C<C^+$;
b) determining a modulation factor ($z_i$), wherein the modulation factor ($z_i$) is a function of volumes ($v_i$) and dilution factors ($d_i$) of the sample in at least part of or all of the (N) compartments and partitioning the sample into the (N) compartments, based at least in part on the modulation factor ($z_i$), wherein at least part of or all of the two or more of the (N) compartments comprise or consist of different sample volumes ($v_i$) and/or different dilution factors ($d_i$) of the sample, wherein (i) represents an index number of the (N) compartments represented by the integers 0 to N−1, and wherein ($v_i$) represents the volume and ($d_i$) represents the dilution factor of the sample in the compartment (i), and wherein the modulation factor ($z_i$) is determined based on a well-defined power sequence, a geometric sequence, an exponential sequence, a polynomial sequence, a distribution in the set of compartments, or a combination thereof, and wherein the set of values of the products ($v_i$) ($d_i$) is determined by a function that is non-uniform over a range of variation of the index (i);
c) measuring a digital signal from two or more of the (N) compartments and assigning to at least part, preferably all compartments a digital value ($k_i$), wherein compartment (i) is assigned a first value ($k_i$), if the compartment (i) comprises or consists of a predetermined threshold number of analyte particles ($m_{tr_i}$) or a predetermined threshold concentration of analyte particles ($c_{tr_i}$), preferably one, two, three or more analyte particles in a compartment, and compartment (i) is assigned a second value ($k_i$), if the compartment (i) comprises or consists of less than the threshold number or concentration of analyte particles indicating the first value,
d) determining an analog value ($\tau_i$) for two or more of the (N) compartments, respectively, based on one or more measurements of signals in compartment (i) and based on at least one of:
a direct measurement of a physical quantity of the sample in the compartment (i);
a resealing of a direct measurement of a physical quantity of the sample in the compartment (i); and
a mathematical calculation on the basis of a set of direct measurements of the sample in the compartment (i),
wherein (i) represents the index number of the compartment represented by an integer 0 to N−1, wherein the analog values ($\tau_i$) depend on the number of analyte particles in the compartment (i) and comprise univocal functions of the number of analyte particles in compartment (i) and wherein at least for one compartment thereof a value ($k_i$) is assigned according to step (c), and
(e) determining the estimate of concentration of analyte particles E(C) as a function of at least a portion of the digital values ($k_i$) assigned in step (c) and at least a portion of the analog values ($\tau_i$) determined in step (d), whereby the measurement of the digital values ($k_i$) allows the analog valves ($\tau_i$) to be determinable without external calibration.

2. The method according to claim 1, wherein the function in step (e) is further based on the predetermined probability distribution ($p_i$ ($m_i$)) of the number of analyte particles in compartment (i).

3. The method according to claim 2, wherein the probability distribution ($p_i(m_i)$) of the number of analyte particles in compartment (i) is a function of properties ($\Gamma_i$) of compartment (i) and/or of properties ($T_i$) of the treatment of compartment (i) and/or of the determinable concentration of analyte particles in compartment (i).

4. The method according to claim 3, wherein the properties ($P_i$) of compartment (i) comprise or consist of the dilution factor ($d_i$) of the sample in compartment (i) and/or the volume ($v_i$) of the sample in compartment (i) and/or of the surface to volume ratio of compartment (i).

5. The method according to claim 3, wherein the other methods of deposition comprise ballistic or more general forced deposition of anayte particles at interferences or in compartments.

6. The method according to claim 1, wherein in step (e) a density of probability ($\rho_i(k_i|C)$) for at least part or all compartments (i) is determined as a function of the probability distribution ($p_i(m_i)$) and part or all values ($k_i$) assigned in step (c) and/or is a function of the probability distribution ($p_i(m_i)$) and part or all analog values ($\tau_i$) determined in step (d).

7. The method according to claim 6, wherein in step (e) the product of the density of probabilities ($\Psi(\{k_i\}|C)=\Pi_i\rho_i(\{k_i\}|C)$) is transferred into the estimate of concentration of analyte particles E(C) and the standard deviation σ(C).

8. The method according to claim 1, wherein the measurements in compartment (i) of step (c) and step (d) are conducted with the same method or with different methods.

9. The method according to claim 8, wherein the measuring method comprises measurement of physical properties selected from the group consisting of light excitation with respect to colour or intensity; electrical conductivity; time of passage of analyte particles through a suitable matrix; amplitude of force exerted on the sample.

10. The method according to claim 9, wherein the light excitation or light absorbance is in the UV range, variable range and/or IR range.

11. The method according to claim 1, wherein the method is applicable to determine the estimate of concentration of analyte particles E(C) of suitable analyte particles selected from the group comprising or consisting of nucleic acids, peptides, proteins, receptors, enzymes, bacteria, pesticides, drugs, steroids, hormones, lipids, sugars, vitamins or any other suitable analyte particles.

12. The method according to claim 11, wherein the other suitable analyte particles further comprise nanoparticles or colloids, or combinations thereof.

13. The method according to claim 1, wherein the method is applicable to quantitation measurements (assays) amplifying the presence of a suitable analyte particle to a measurable signal, preferably wherein the analyte particles are amplified by means of Polymerase Chain Reaction (PCR), more preferably comprising cyclic temperature variation; loop-mediated isothermal amplification (LAMP); rolling circle amplification (RCA); cascade rolling circle amplification (Cascade RCA); helicase-dependent amplification; nucleic acid sequence based amplification (NASBA); nicking enzyme amplification reaction (NEAR); (single-molecule) enzyme-linked immunoabsorbent assay [(digital) ELISA]; electrochemiluminescence immunoassay (ECLIA); competitive or non-competitive immunoassays; chemical chain reactions; avalanche reactions; or any other procedure for amplification of the presence of a analyte particle to a measurable signal, wherein the amplitude of the signal is a univocal function of the concentration of analyte particles; or a combination thereof.

14. An apparatus for use in determining a concentration of analyte particles in accordance with claim 1, characterized in that the apparatus is configured to:
  a) determine the number (N) of separate compartments, wherein the number (N) is smaller or equal to the value of the function:

$$N_{MAX} = B \cdot \ln\left(\frac{C^+}{C^-}\right)/\sigma_{MAX}^2$$

wherein (A) represents a real number equal to 6 or less, preferably 1 or less, more preferably 0.5 and even more preferably 0.2;
  wherein ($C^+$) represents an upper limit of the interval of concentration (C) to be estimated by the method;
  wherein ($C^-$) represents a lower limit of the interval of concentration (C) to be estimated by the method; and
  wherein ($\sigma_{MAX}$) represents a maximum allowable relative standard deviation of the estimate of concentration (C) of analyte particles, wherein $C^- < C < C^+$;
  b) determine a modulation factor ($z_i$), wherein the modulation factor ($z_i$) is a function of volumes ($v_i$) and dilution factors ($d_i$) of the sample in at least part of or all of the (N) compartments and partitioning the sample into the (N) compartments, based at least in part on the modulation factor ($z_i$), wherein at least part of or all of the two or more of the (N) compartments comprise or consist of different sample volumes ($v_i$) and/or different dilution factors ($d_i$) of the sample, wherein (i) represents an index number of the (N) compartments represented by the integers 0 to N−1, and wherein ($v_i$) represents the volume and ($d_i$) represents the dilution factor of the sample in the compartment (i), and wherein the modulation factor ($z_i$) is determined based on a well-defined power sequence, a geometric sequence, an exponential sequence, a polynomial sequence, a distribution in the set of compartments, or a combination thereof, and wherein the set of values of the products ($v_i$) ($d_i$) is determined by a function that is non-uniform over a range of variation of the index (i);
  c) measuring a digital signal from two or more of the (N) compartments and assigning to at least part, preferably all compartments a digital value ($k_i$), compartment (i) is assigned a first value ($k_i$), if the compartment (i) comprises or consists of a predetermined threshold number of analyte particles ($m_{tr_i}$) or a predetermined threshold concentration of analyte particles ($c_{tr_i}$), preferably one, two, three or more analyte particles in a compartment, and compartment (i) is assigned a second value ($k_i$), if the compartment (i) comprises or consists of less than the threshold number or concentration of analyte particles indicating the first value,
  d) determining an analog value ($T_i$) for two or more of the (N) compartments, respectively, based on one or more measurements of signals in compartment (i) and based on at least one of:
    a direct measurement of a physical quantity of the sample in the compartment (i);
    a resealing of a direct measurement of a physical quantity of the sample in the compartment (i); and
    a mathematical calculation on the basis of a set of direct measurements of the sample in the compartment (i),
    wherein (i) represents the index number of the compartment represented by an integer 0 to N−1, wherein the analog values ($\tau_i$) depend on the number of analyte particles in the compartment (i) and comprise univocal functions of the number of analyte particles in compartment (i) and wherein at least for one compartment thereof a value ($k_i$) is assigned according to step (c), and
  e) determining the estimate of concentration of analyte particles E(C) as a function of at least a portion of the values ($k_i$) assigned in step (c) and at least a portion of the analog values ($\tau_i$) determined in step (d), whereby the measurement of the digital values ($k_i$) allows the analog valves ($\tau_i$) to be determinable without external calibration.

15. A method for determining an estimate of a concentration of analyte particles E(C), wherein the analyte particles of a sample of predetermined volume are divided into a number (N) of two or more compartments, at least part of the analyte particles that are present in any of the (N) compartments provide for a measurable signal and the estimated concentration of analyte particles E(C) is a function of the measured signals, characterized in that the method comprises:
  a) determining the number (N) of separate compartments, wherein the number (N) is smaller or equal to the value of the function:

$$N_{MAX} = A \cdot \ln\left(\frac{C^+}{C^-}\right)/\sigma_{MAX}^2$$

wherein (A) represents a real number equal to 6 or less, preferably 1 or less, more preferably 0.5 and even more preferably 0.2;
  wherein ($C^+$) represents an upper limit of the interval of concentration (C) to be estimated by the method;
  wherein ($C^-$) represents a lower limit of the interval of concentration (C) to be estimated by the method; and
  wherein ($\sigma_{MAX}$) represents a maximum allowable relative standard deviation of the estimate of concentration (C) of analyte particles, wherein $C^- < C < C^+$;
  b) determining a modulation factor ($z_i$), wherein the modulation factor ($z_i$) is a function of volumes ($v_i$) and dilution factors ($d_i$) of the sample in at least part of or all of the (N) compartments and partitioning the sample into the (N) compartments, based at least in part on the modulation factor ($z_i$), wherein at least part of or all of the two or more of the (N) compartments comprise or consist of different sample volumes ($v_i$) and/or different dilution factors ($d_i$) of the sample, wherein (i) represents an index number of the (N) compartments represented by the integers 0 to N−1, and wherein ($v_i$)

represents the volume and ($d_i$) represents the dilution factor of the sample in the compartment (i), and wherein the modulation factor ($z_i$) is determined based on a well-defined power sequence, a geometric sequence, an exponential sequence, a polynomial sequence, a distribution in the set of compartments, or a combination thereof, and wherein the set of values of the products ($v_i$) ($d_i$) is determined by a function that is non-uniform over a range of variation of the index (i);

(c) measuring a digital signal from two or more of the (N) compartments and assigning to at least part, preferably all compartments a digital value ($k_i$), wherein compartment (i) is assigned a first value ($k_i$), if the compartment (i) comprises or consists of a predetermined threshold number of analyte particles ($m_{tr_i}$) or a predetermined threshold concentration of analyte particles ($c_{tr_i}$), preferably one, two, three or more analyte particles in a compartment, and compartment (i) is assigned a second value ($k_i$), if the compartment (i) comprises or consists of less than the threshold number or concentration of analyte particles indicating the first value, (d) determining an analog value ($\tau_i$) for two or more of the (N) compartments, respectively, based on one or more measurements of signals in compartment (i) and based on at least one of:

a direct measurement of a physical quantity of the sample in the compartment (i);

a resealing of a direct measurement of a physical quantity of the sample in the compartment (i); and a mathematical calculation on the basis of a set of direct measurements of the sample in the compartment (i), wherein (i) represents the index number of the compartment represented by an integer 0 to N−1, wherein the analog values ($\tau_i$) depend on the number of analyte particles in the compartment (i) and comprise univocal functions of the number of analyte particles in compartment (i), wherein the values ($\tau_i$) belong to the ordered set, and wherein at least for one compartment thereof a value ($k_i$) is assigned according to step (c), and (e) determining the estimate of concentration of analyte particles E(C) as a function of at least a portion of the values ($k_i$) assigned in step (c) and at least, a portion of the analog values ($\tau_i$) determined in step (d), whereby the measurement of the digital values ($k_i$) allows the analog valves ($\tau_i$) to be determinable without external calibration.

* * * * *

UNITED STATES PATENT AND TRADEMARK OFFICE
CERTIFICATE OF CORRECTION

Page 1 of 1

PATENT NO. : 10,209,246 B2
APPLICATION NO. : 14/411303
DATED : February 19, 2019
INVENTOR(S) : Debski et al.

It is certified that error appears in the above-identified patent and that said Letters Patent is hereby corrected as shown below:

In the Claims

Claim 14, Column 34, Line 10, "resealing" should be --rescaling--.

Claim 15, Column 36, Line 3, "resealing" should be --rescaling--.

Signed and Sealed this
Eighteenth Day of June, 2019

Andrei Iancu
*Director of the United States Patent and Trademark Office*

UNITED STATES PATENT AND TRADEMARK OFFICE
CERTIFICATE OF CORRECTION

PATENT NO.       : 10,209,246 B2
APPLICATION NO.  : 14/411303
DATED            : February 19, 2019
INVENTOR(S)      : Debski et al.

It is certified that error appears in the above-identified patent and that said Letters Patent is hereby corrected as shown below:

In the Claims

Claim 1, Column 31, Line 61, "a resealing" should be --a rescaling--.

Claim 1, Column 32, Line 11, "analog valves ($\tau_i$)" should be --analog values ($\tau_i$)--.

Claim 4, Column 32, Line 24, "($P_i$)" should be --($\Gamma_i$)--.

Claim 5, Column 32, Line 30, "interferences" should be --interfaces--.

Claim 14, Column 33, Line 25, "$N_{MAX} = B \cdot \ln\left(\frac{C^+}{C^-}\right)/\sigma^2_{MAX}$" should be --$N_{MAX} = A \cdot \ln\left(\frac{C^+}{C^-}\right)/\sigma^2_{MAX}$--.

Claim 14, Column 34, Line 4, "($T_i$)" should be --($\tau_i$)--.

Claim 14, Column 34, Line 27, "analog valves ($\tau_i$)" should be --analog values ($\tau_i$)--.

Claim 15, Column 36, Line 21, "analog valves ($\tau_i$)" should be --analog values ($\tau_i$)--.

Signed and Sealed this
Twenty-first Day of April, 2020

Andrei Iancu
*Director of the United States Patent and Trademark Office*